(12) United States Patent
Grimes et al.

(10) Patent No.: US 6,437,219 B1
(45) Date of Patent: Aug. 20, 2002

(54) NUCLEIC ACIDS ENCODING SUCROSE-BINDING PROTEINS

(75) Inventors: Howard D. Grimes; Wun S. Chao, both of Pullman, WA (US)

(73) Assignee: Washington State University Research Foundation, Pullman, WA (US)

( * ) Notice: Subject to any disclaimer, the term of this patent is extended or adjusted under 35 U.S.C. 154(b) by 0 days.

(21) Appl. No.: 09/424,283

(22) PCT Filed: May 21, 1998

(86) PCT No.: PCT/US98/10465

§ 371 (c)(1),
(2), (4) Date: Nov. 19, 1999

(87) PCT Pub. No.: WO98/53086

PCT Pub. Date: Nov. 26, 1998

Related U.S. Application Data

(60) Provisional application No. 60/047,568, filed on May 22, 1997.

(51) Int. Cl.[7] .......................... A01H 5/00; C12N 15/29; C12N 15/52; C12N 15/82; C12P 19/04
(52) U.S. Cl. ...................... 800/284; 800/278; 800/298; 536/23.2; 536/236; 435/320.1; 435/419
(58) Field of Search .............................. 536/23.2, 23.6, 536/24.1; 800/278, 284, 298; 435/419, 320.1

(56) References Cited

FOREIGN PATENT DOCUMENTS

WO    WO 94/00574    1/1994

OTHER PUBLICATIONS

Grisvard, J. et al., "A splice site mutation gives rise to a mutant of the C4 plant Amaranthus edulis deficient in phosphoenolpyruvate carboxylase activity." 1998, Gene, vol. 213, pp. 31–35.*

Hill, M. A. and Preiss, J. "Functional Analysis of Conserved Histidines in ADP–Glucose Pyrophosphorylase from Escherichia coli." 1998, Biochemical and Biophysical Res. Comm., vol. 244, pp. 573–577.*

Burgess, W. H. et al., "Possible Dissociation of the Heparin–binding and Mitogenic Activities of Heparin–binding . . . by Site–directed Mutagenesis of a Single Lysine Residue." 1990, The J. of Cell Biology, vol. 111, pp. 2129–2138.*

Bowie, J. U. et al., "Deciphering the Message in Protein Sequences: Tolerance to Amino Acid Substitutions." 1990, Science, vol. 247, pp. 1306–1310.*

Broun, P. et al., "Catalytic Plasticity of Fatty Acid Modification Enzymes Underlying Chemical Diversity of Plant Lipids." 1998, Science, vol. 282, pp. 1315–1317.*

Lazar, E. et al., "Transforming Growth Factor a: Mutation of Aspartic Acid 47 and Leucine 48 Results in Different Biological Activities." 1988, Molecular and Cellular Biology, vol. 8, pp. 1247–1252.*

Visser, R. et al., Molecular Cloning and Partial Characterization of the Gene for Granule–Bound Starch Synthase from a Wildtype and an Amulose–Free Potato (*Solanum tuberosum* L.), Plant Science, 64:185–192, 1989.

Visser, R., et al., Expression of a Chimaeric Granule–Bound Starch Synthase–GUS Gene in Transgenic Potato Plants, *Plant Mol. Biol.*, 17:691–699, 1991.

Riesmeier, J., et al., Isolation and Characterization of a Sucrose Carrier cDNA from Spinach by Functional Expression in Yeast, *EMBO Jour.*, 11:4705–4713, 1992.

Grimes, H., et al., A 62–kD Sucrose Binding Protein is Expressed and Localized in Tissues Actively Engaged in Sucrose Transport, *Plant Cell*, 4:1561–1574, 1992.

Riesmeier, J., et al., Potato Sucrose Transporter Expression in Minor Veins Indicates a Role in Phloem Loading, *Plant Cel.*, 5:1591–1598, 1993.

Saurer, N., et al., Sugar Transport Across the Plasma Membranes of Higher Plants, *Plant Mol. Biol.*, 26:1671–1679, 1994.

Gahrtz, M., et al., A Phloem–Specific Sucrose–H[+]Symporter from *Plantago major* L. Supports the Model of Apoplastic Phloem Loading, *Plant. J.*, 6:697–706, 1994.

Sauer, N. and Stolz. J., SUC1 and SUC2: Two Sucrose Transporters from *Arabidopsis thaliana*; Expression and Characterization in Baker's Yeast and Identification of the Histidine–Tagged Protein, *Plant J.*, 6:67–77, 1994.

Overvoorde, P. and Grimes, H., Topographical Analysis of the Plasma Membrane–Associated Sucrose Binding Protein from Soybean, *J. Biol. Chem.*, 269:15154–15161, 1994.

Stolz, J., et al., Rapid Purification of a Functionally Active Plant Sucrose Carrier from Transgenic Yeast Using a Bacterial Biotin Acceptor Domain, *FEBS Lett.*, 377:167–171, 1995.

Weig, A and Komor, E., An Active Sucrose Carrier (Scr1) that is Predominantly Expressed in the Seedling of *Ricinus communis* L., *Plant. Phys.*, 147:685–690, 1996.

(List continued on next page.)

Primary Examiner—David T. Fox
Assistant Examiner—Anne Kubelik
(74) Attorney, Agent, or Firm—Klarquist Sparkman, LLP

(57) ABSTRACT

A cDNA encoding a plant sucrose binding protein (SBP) is provided, together with modified SBPs having enhanced sucrose uptake activity in a yeast assay system. Nucleic acid vectors, transgenic cell and transgenic plants having modified sucrose uptake activity are also provided. The invention also relates to promoter sequences useful for controlling expression of transgenes in plants, including SBP transgenes.

4 Claims, 3 Drawing Sheets

OTHER PUBLICATIONS

Gahrtz, M., et al., Expression of the PmSUC1 Sucrose Carrier Gene from *Plantago major* L. is induced During Seed Development, *Plant J.*, 9:93–100, 1996.

Overvoorde, P., et al., A Soybean Sucrose Binding Protein Independently Mediates Nonsaturable Sucrose Uptake in Yeast, *Plant Cell*, 8:271–280, 1996.

Overvoorde, P., et al., A Plasma Membrane Sucrose–Binding Protein That Mediates Sucrose Uptake Shares Structural and Sequence Similarity with Seed Storage Proteins but Remains Functionally Distinct, *J. Biol. Chem.*, 272:15898–15904, 1997.

Hirose, T., et al., cDNA Cloning and Tissue Specific Expression of a Gene for Sucrose Transporter from Rice (*Oryza sativa* L.), *Plant Cell Physiol.*, 38:1389–1396, 1997.

Chao., W., et al., Functional and Structural Analysis of Sucrose Binding Protein in a Heterologous Yeast System, *Supp. Plant Physiol.*, 114:955, 1997.

Lu, M–Y. J., et al., Site–Directed Mutagenesis of HIS71 in the Proton–Sucrose Symporter, *Supp. Plant Physiol.*, 114:958, 1997

* cited by examiner

```
sbp1  MAMRTKLSLA  IFFFFLLALF  SNLAFGKCKE  TEVEEEDPEL      40
sbp2  MATRAKLSLA  IFLFFLLALI  SNLALGKLKE  TEV.EEDPEL      39 sbp1  VTCKHQCQQQ  QQYTEGDKRV  CLQSCDRYHR  MKQEREKQIQ      80
sbp2  VTCKHQCQQQ  RQYTESDKRT  CLQQCD...S  MKQEREKQVE      76 sbp1  EETREKKEEE  SREREEEQQE  QHEEQDENPY  IFEEDKDFET     120
sbp2  EETREKE...  ....EEHQEQ  HEEEEDENPY  VFEEDKDFST     109

*   *              *          *
sbp1  RVETEGGRIR  VLKKFTEKSK  LLQGIENFRL  AILEARAHTF     160
sbp2  RVETEGGSIR  VLKKFTEKSK  LLQGIENFRL  AILEARAHTF     149
                     QR                              P

*    *          *
sbp1  VSPRHFDSEV  VFFNIKGRAV  LGLVSESETE  KITLEPGDMI     200
sbp2  VSPRHFDSEV  VLFNIKGRAV  LGLVRESETE  KITLEPGDMI     189

*    *              *                   *
sbp1  HIPAGTPLYI  VNRDENDKLF  LAMLHIPVSV  STPGKFEEFF     240
sbp2  HIPAGTPLYI  VNRDENEKLL  LAMLHIP..V  STPGKFEEFF     227

**
sbp1  GPGGRDPESV  LSAFSWNVLQ  AALQTPKGKL  EKLFDQQNEG     280
sbp2  GPGGRDPESV  LSAFSWNVLQ  AALQTPKGKL  ERLFNQQNEG     267

*
sbp1  SIFAISREQV  RALAPTKKSS  WWPFGGESKP  QFNIFSKRPT     320
sbp2  SIFKISRERV  RALAPTKKSS  WWPFGGESKA  QFNIFSKRPT     307

*   *                                *
sbp1  ISNGYGRLTE  VGPDDDEKSW  LQRLNLMLTF  TNITQRSMST     360
sbp2  FSNGYGRLTE  VGP.DDEKSW  LQRLNLMLTF  TNITQRSMST     346
                                                  G
```

FIG. 1(a)

```
              *                    *
sbp1   IHYNSHATKI   ALVIDGRGHL   QISCPHMSSR   SSHSKHDKSS    400
sbp2   IHYNSHATKI   ALVMDGRGHL   QISCPHMSSR   SD.SKHDKSS    385
       P

*            *             *
sbp1   PSYHRISSDL   KPGMVFVVPP   GHPFVTIASN   KENLLMICFE    440
sbp2   PSYHRISADL   KPGMVFVVPP   GHPFVTIASN   KENLLIICFE    425

*            *             *  *
sbp1   VNARDNKKFT   FAGKDNIVSS   LDNVAKELAF   NYPSEMVNGV    480
sbp2   VNVRDNKKFT   FAGKDNIVSS   LDNVAKELAF   NYPSEMVNGV    465 sbp1   FLLQRFLERK   LIGRLYHLPH   KDRKESFFFP   FELPREERGR    520
sbp2   ..........   ..........   SERKESLFFP   FELPSEERGR    485 sbp1   RADA*    524
sbp2   RAVA*    489
```

FIG. 1(b)

SEQUENCE LISTING

```
<160> NUMBER OF SEQ ID NOS:  15

<210> SEQ ID NO 1
<211> LENGTH: 524
<212> TYPE: PRT
<213> ORGANISM: Glycine max

<400> SEQUENCE: 1

Met Gly Met Arg Thr Lys Leu Ser Leu Ala Ile Phe Phe Phe Leu
  1               5                  10                  15

Leu Ala Leu Phe Ser Asn Leu Ala Phe Gly Lys Cys Lys Glu Thr Glu
                 20                  25                  30

Val Glu Glu Glu Asp Pro Glu Leu Val Thr Cys Lys His Gln Cys Gln
             35                  40                  45

Gln Gln Gln Gln Tyr Thr Glu Gly Asp Lys Arg Val Cys Leu Gln Ser
         50                  55                  60

Cys Asp Arg Tyr His Arg Met Lys Gln Glu Arg Glu Lys Gln Ile Gln
 65                  70                  75                  80

Glu Glu Thr Arg Glu Lys Lys Glu Glu Glu Ser Arg Glu Arg Glu Glu
                 85                  90                  95

Glu Gln Gln Glu Gln His Glu Glu Gln Asp Glu Asn Pro Tyr Ile Phe
            100                 105                 110

Glu Glu Asp Lys Asp Phe Glu Thr Arg Val Glu Thr Glu Gly Gly Arg
        115                 120                 125

Ile Arg Val Leu Lys Lys Phe Thr Glu Lys Ser Lys Leu Leu Gln Gly
    130                 135                 140

Ile Glu Asn Phe Arg Leu Ala Ile Leu Glu Ala Arg Ala His Thr Phe
145                 150                 155                 160

Val Ser Pro Arg His Phe Asp Ser Glu Val Val Phe Phe Asn Ile Lys
                165                 170                 175

Gly Arg Ala Val Leu Gly Leu Val Ser Glu Ser Glu Thr Glu Lys Ile
            180                 185                 190

Thr Leu Glu Pro Gly Asp Met Ile His Ile Pro Ala Gly Thr Pro Leu
        195                 200                 205

Tyr Ile Val Asn Arg Asp Glu Asn Asp Lys Leu Phe Leu Ala Met Leu
```

-continued

```
            210                 215                 220
His Ile Pro Val Ser Val Ser Thr Pro Gly Lys Phe Glu Glu Phe Phe
225                 230                 235                 240

Ala Pro Gly Gly Arg Asp Pro Glu Ser Val Leu Ser Ala Phe Ser Trp
                245                 250                 255

Asn Val Leu Gln Ala Ala Leu Gln Thr Pro Lys Gly Lys Leu Glu Asn
            260                 265                 270

Val Phe Asp Gln Gln Asn Glu Gly Ser Ile Phe Arg Ile Ser Arg Glu
        275                 280                 285

Gln Val Arg Ala Leu Ala Pro Thr Lys Lys Ser Ser Trp Trp Pro Phe
    290                 295                 300

Gly Gly Glu Ser Lys Pro Gln Phe Asn Ile Phe Ser Lys Arg Pro Thr
305                 310                 315                 320

Ile Ser Asn Gly Tyr Gly Arg Leu Thr Glu Val Gly Pro Asp Asp
                325                 330                 335

Glu Lys Ser Trp Leu Gln Arg Leu Asn Leu Met Leu Thr Phe Thr Asn
                340                 345                 350

Ile Thr Gln Arg Ser Met Ser Thr Ile His Tyr Asn Ser His Ala Thr
            355                 360                 365

Lys Ile Ala Leu Val Ile Asp Gly Arg Gly His Leu Gln Ile Ser Cys
370                 375                 380

Pro His Met Ser Ser Arg Ser Ser His Ser Lys His Asp Lys Ser Ser
385                 390                 395                 400

Pro Ser Tyr His Arg Ile Ser Ser Asp Leu Lys Pro Gly Met Val Phe
                405                 410                 415

Val Val Pro Pro Gly His Pro Phe Val Thr Ile Ala Ser Asn Lys Glu
                420                 425                 430

Asn Leu Leu Met Ile Cys Phe Glu Val Asn Ala Arg Asp Asn Lys Lys
            435                 440                 445

Phe Thr Phe Ala Gly Lys Asp Asn Ile Val Ser Ser Leu Asp Asn Val
450                 455                 460

Ala Lys Glu Leu Ala Phe Asn Tyr Pro Ser Glu Met Val Asn Gly Val
465                 470                 475                 480

Phe Leu Leu Gln Arg Phe Leu Glu Arg Lys Leu Ile Gly Arg Leu Tyr
                485                 490                 495

His Leu Pro His Lys Asp Arg Lys Glu Ser Phe Phe Pro Phe Glu
                500                 505                 510

Leu Pro Arg Glu Glu Arg Gly Arg Arg Ala Asp Ala
            515                 520

<210> SEQ ID NO 2
<211> LENGTH: 444
<212> TYPE: PRT
<213> ORGANISM: Glycine max

<400> SEQUENCE: 2

Met Gly Met Arg Thr Lys Leu Ser Leu Ala Ile Phe Phe Phe Phe Leu
 1               5                  10                  15

Leu Ala Leu Phe Ser Asn Leu Ala Phe Gly Lys Cys Lys Glu Thr Glu
            20                  25                  30

Val Glu Glu Glu Asp Pro Glu Leu Val Thr Cys Lys His Gln Cys Gln
        35                  40                  45

Gln Gln Gln Gln Tyr Thr Glu Gly Asp Lys Arg Val Cys Leu Gln Ser
    50                  55                  60
```

```
Cys Asp Arg Tyr His Arg Met Lys Gln Glu Arg Glu Lys Gln Ile Gln
 65                  70                  75                  80

Glu Glu Thr Arg Glu Lys Lys Glu Glu Glu Ser Arg Glu Arg Glu Glu
             85                  90                  95

Glu Gln Gln Glu Gln His Glu Gln Gln Asp Glu Asn Pro Tyr Ile Phe
        100                 105                 110

Glu Glu Asp Lys Asp Phe Glu Thr Arg Val Glu Thr Glu Gly Gly Arg
        115                 120                 125

Ile Arg Val Leu Lys Lys Phe Thr Glu Lys Ser Lys Leu Leu Gln Gly
130                 135                 140

Ile Glu Asn Phe Arg Leu Ala Ile Leu Glu Ala Arg Ala His Thr Phe
145                 150                 155                 160

Val Ser Pro Arg His Phe Asp Ser Glu Val Phe Phe Asn Ile Lys
                165                 170                 175

Gly Arg Ala Val Leu Gly Leu Val Ser Glu Ser Glu Thr Glu Lys Ile
                180                 185                 190

Thr Leu Glu Pro Gly Asp Met Ile His Ile Pro Ala Gly Thr Pro Leu
            195                 200                 205

Tyr Ile Val Asn Arg Asp Glu Asn Asp Lys Leu Phe Leu Ala Met Leu
210                 215                 220

His Ile Pro Val Ser Val Ser Thr Pro Gly Lys Phe Glu Glu Phe Phe
225                 230                 235                 240

Ala Pro Gly Gly Arg Asp Pro Glu Ser Val Leu Ser Ala Phe Ser Trp
                245                 250                 255

Asn Val Leu Gln Ala Ala Leu Gln Thr Pro Lys Gly Lys Leu Glu Asn
            260                 265                 270

Val Phe Asp Gln Gln Asn Glu Gly Ser Ile Phe Arg Ile Ser Arg Glu
        275                 280                 285

Gln Val Arg Ala Leu Ala Pro Thr Lys Lys Ser Ser Trp Trp Pro Phe
        290                 295                 300

Gly Gly Glu Ser Lys Pro Gln Phe Asn Ile Phe Ser Lys Arg Pro Thr
305                 310                 315                 320

Ile Ser Asn Gly Tyr Gly Arg Leu Thr Glu Val Gly Pro Asp Asp Asp
                325                 330                 335

Glu Lys Ser Trp Leu Gln Arg Leu Asn Leu Met Leu Thr Phe Thr Asn
            340                 345                 350

Ile Thr Gln Arg Ser Met Ser Thr Ile His Tyr Asn Ser His Ala Thr
            355                 360                 365

Lys Ile Ala Leu Val Ile Asp Gly Arg Gly His Leu Gln Ile Ser Cys
370                 375                 380

Pro His Met Ser Ser Arg Ser Ser His Ser Lys His Asp Lys Ser Ser
385                 390                 395                 400

Pro Ser Tyr His Arg Ile Ser Ser Asp Leu Lys Pro Gly Met Val Phe
                405                 410                 415

Val Val Pro Pro Gly His Pro Phe Val Thr Ile Ala Ser Asn Lys Glu
            420                 425                 430

Asn Leu Leu Met Ile Cys Phe Glu Val Asn Ala Arg
            435                 440
```

<210> SEQ ID NO 3
<211> LENGTH: 489
<212> TYPE: PRT
<213> ORGANISM: Glycine max

<400> SEQUENCE: 3

-continued

```
Met Ala Thr Arg Ala Lys Leu Ser Leu Ala Ile Phe Leu Phe Phe Leu
 1               5                  10                  15
Leu Ala Leu Ile Ser Asn Leu Ala Leu Gly Lys Leu Lys Glu Thr Glu
             20                  25                  30
Val Glu Glu Asp Pro Glu Leu Val Thr Cys Lys His Gln Cys Gln Gln
         35                  40                  45
Gln Arg Gln Tyr Thr Glu Ser Asp Lys Arg Thr Cys Leu Gln Gln Cys
     50                  55                  60
Asp Ser Met Lys Gln Glu Arg Glu Lys Gln Val Glu Glu Glu Thr Arg
 65                  70                  75                  80
Glu Lys Glu Glu Glu His Gln Glu Gln His Glu Glu Glu Glu Asp Glu
                 85                  90                  95
Asn Pro Tyr Val Phe Glu Glu Asp Lys Asp Phe Ser Thr Arg Val Glu
             100                 105                 110
Thr Glu Gly Gly Ser Ile Arg Val Leu Lys Lys Phe Thr Glu Lys Ser
             115                 120                 125
Lys Leu Leu Gln Gly Ile Glu Asn Phe Arg Leu Ala Ile Leu Glu Ala
             130                 135                 140
Arg Ala His Thr Phe Val Ser Pro Arg His Phe Asp Ser Glu Val Val
145                 150                 155                 160
Leu Phe Asn Ile Lys Gly Arg Ala Val Leu Gly Leu Val Arg Glu Ser
                 165                 170                 175
Glu Thr Glu Lys Ile Thr Leu Glu Pro Gly Asp Met Ile His Ile Pro
             180                 185                 190
Ala Gly Thr Pro Leu Tyr Ile Val Asn Arg Asp Glu Asn Glu Lys Leu
             195                 200                 205
Leu Leu Ala Met Leu His Ile Pro Val Ser Thr Pro Gly Lys Phe Glu
210                 215                 220
Glu Phe Phe Gly Pro Gly Gly Arg Asp Pro Glu Ser Val Leu Ser Ala
225                 230                 235                 240
Phe Ser Trp Asn Val Leu Gln Ala Ala Leu Gln Thr Pro Lys Gly Lys
                 245                 250                 255
Leu Glu Arg Leu Phe Asn Gln Gln Asn Glu Gly Ser Ile Phe Lys Ile
             260                 265                 270
Ser Arg Glu Arg Val Arg Ala Leu Ala Pro Thr Lys Lys Ser Ser Trp
         275                 280                 285
Trp Pro Phe Gly Gly Glu Ser Lys Ala Gln Phe Asn Ile Phe Ser Lys
         290                 295                 300
Arg Pro Thr Phe Ser Asn Gly Tyr Gly Arg Leu Thr Glu Val Gly Pro
305                 310                 315                 320
Asp Asp Glu Lys Ser Trp Leu Gln Arg Leu Asn Leu Met Leu Thr Phe
                 325                 330                 335
Thr Asn Ile Thr Gln Arg Ser Met Ser Thr Ile His Tyr Asn Ser His
                 340                 345                 350
Ala Thr Lys Ile Ala Leu Val Met Asp Gly Arg Gly His Leu Gln Ile
             355                 360                 365
Ser Cys Pro His Met Ser Ser Arg Ser Asp Ser Lys His Asp Lys Ser
         370                 375                 380
Ser Pro Ser Tyr His Arg Ile Ser Ala Asp Leu Lys Pro Gly Met Val
385                 390                 395                 400
Phe Val Val Pro Pro Gly His Pro Phe Val Thr Ile Ala Ser Asn Lys
                 405                 410                 415
```

```
Glu Asn Leu Leu Ile Ile Cys Phe Glu Val Asn Val Arg Asp Asn Lys
                420                 425                 430

Lys Phe Thr Phe Ala Gly Lys Asp Asn Ile Val Ser Ser Leu Asp Asn
            435                 440                 445

Val Ala Lys Glu Leu Ala Phe Asn Tyr Pro Ser Glu Met Val Asn Gly
        450                 455                 460

Val Ser Glu Arg Lys Glu Ser Leu Phe Phe Pro Phe Glu Leu Pro Ser
465                 470                 475                 480

Glu Glu Arg Gly Arg Arg Ala Val Ala
                485

<210> SEQ ID NO 4
<211> LENGTH: 409
<212> TYPE: PRT
<213> ORGANISM: Glycine max

<400> SEQUENCE: 4

Met Ala Thr Arg Ala Lys Leu Ser Leu Ala Ile Phe Leu Phe Phe Leu
  1               5                  10                  15

Leu Ala Leu Ile Ser Asn Leu Ala Leu Gly Lys Leu Lys Glu Thr Glu
             20                  25                  30

Val Glu Glu Asp Pro Glu Leu Val Thr Cys Lys His Gln Cys Gln Gln
         35                  40                  45

Gln Arg Gln Tyr Thr Glu Ser Asp Lys Arg Thr Cys Leu Gln Gln Cys
     50                  55                  60

Asp Ser Met Lys Gln Glu Arg Glu Lys Gln Val Glu Glu Glu Thr Arg
 65                  70                  75                  80

Glu Lys Glu Glu Glu His Gln Glu Gln His Glu Glu Glu Glu Asp Glu
                 85                  90                  95

Asn Pro Tyr Val Phe Glu Glu Asp Lys Asp Phe Ser Thr Arg Val Glu
            100                 105                 110

Thr Glu Gly Gly Ser Ile Arg Val Leu Lys Lys Phe Thr Glu Lys Ser
        115                 120                 125

Lys Leu Leu Gln Gly Ile Glu Asn Phe Arg Leu Ala Ile Leu Glu Ala
    130                 135                 140

Arg Ala His Thr Phe Val Ser Pro Arg His Phe Asp Ser Glu Val Val
145                 150                 155                 160

Leu Phe Asn Ile Lys Gly Arg Ala Val Leu Gly Leu Val Arg Glu Ser
                165                 170                 175

Glu Thr Glu Lys Ile Thr Leu Glu Pro Gly Asp Met Ile His Ile Pro
            180                 185                 190

Ala Gly Thr Pro Leu Tyr Ile Val Asn Arg Asp Glu Asn Glu Lys Leu
        195                 200                 205

Leu Leu Ala Met Leu His Ile Pro Val Ser Thr Pro Gly Lys Phe Glu
    210                 215                 220

Glu Phe Phe Gly Pro Gly Gly Arg Asp Pro Glu Ser Val Leu Ser Ala
225                 230                 235                 240

Phe Ser Trp Asn Val Leu Gln Ala Ala Leu Gln Thr Pro Lys Gly Lys
                245                 250                 255

Leu Glu Arg Leu Phe Asn Gln Gln Asn Glu Gly Ser Ile Phe Lys Ile
            260                 265                 270

Ser Arg Glu Arg Val Arg Ala Leu Ala Pro Thr Lys Lys Ser Ser Trp
        275                 280                 285

Trp Pro Phe Gly Gly Glu Ser Lys Ala Gln Phe Asn Ile Phe Ser Lys
    290                 295                 300
```

```
Arg Pro Thr Phe Ser Asn Gly Tyr Gly Arg Leu Thr Glu Val Gly Pro
305                 310                 315                 320

Asp Asp Glu Lys Ser Trp Leu Gln Arg Leu Asn Leu Met Leu Thr Phe
            325                 330                 335

Thr Asn Ile Thr Gln Arg Ser Met Ser Thr Ile His Tyr Asn Ser His
            340                 345                 350

Ala Thr Lys Ile Ala Leu Val Met Asp Gly Arg Gly His Leu Gln Ile
            355                 360                 365

Ser Cys Pro His Met Ser Ser Arg Ser Asp Ser Lys His Asp Lys Ser
        370                 375                 380

Ser Pro Ser Tyr His Arg Ile Ser Ala Asp Leu Lys Pro Gly Met Val
385                 390                 395                 400

Phe Val Val Pro Pro Gly His Pro Phe
                405

<210> SEQ ID NO 5
<211> LENGTH: 1924
<212> TYPE: DNA
<213> ORGANISM: Glycine max
<220> FEATURE:
<221> NAME/KEY: CDS
<222> LOCATION: (119)..(1588)

<400> SEQUENCE: 5
tgtaaaacga cggccagtga attgtaatac gactcactat agggcgaatt gggtaccggg      60
ccccccctcg aggtcgacgg tatcgataag cttgattttg ttcctcactg acctcacc      118 atg gcg acc aga gcc aag ctt tct tta gct atc ttc ctt ttc ttt ctt      166
Met Ala Thr Arg Ala Lys Leu Ser Leu Ala Ile Phe Leu Phe Phe Leu
  1               5                  10                  15 tta gcc ttg att tca aac cta gcc ttg ggc aaa ctt aaa gaa acc gag      214
Leu Ala Leu Ile Ser Asn Leu Ala Leu Gly Lys Leu Lys Glu Thr Glu
             20                  25                  30 gtc gaa gaa gat ccc gag ctc gta aca tgc aaa cac cag tgc caa cag      262
Val Glu Glu Asp Pro Glu Leu Val Thr Cys Lys His Gln Cys Gln Gln
         35                  40                  45 caa cgg caa tac act gag agt gac aag cga aca tgc ttg caa caa tgt      310
Gln Arg Gln Tyr Thr Glu Ser Asp Lys Arg Thr Cys Leu Gln Gln Cys
     50                  55                  60 gac agt atg aag caa gag cga gag aaa caa gtc gaa gag gaa act cgc      358
Asp Ser Met Lys Gln Glu Arg Glu Lys Gln Val Glu Glu Glu Thr Arg
 65                  70                  75                  80 gag aag gaa gaa gaa cat caa gag cag cat gag gag gag gaa gac gaa      406
Glu Lys Glu Glu Glu His Gln Glu Gln His Glu Glu Glu Glu Asp Glu
                 85                  90                  95 aat ccc tac gtt ttt gaa gaa gat aag gat ttt tcg acc aga gtc gaa      454
Asn Pro Tyr Val Phe Glu Glu Asp Lys Asp Phe Ser Thr Arg Val Glu
            100                 105                 110 aca gaa ggt ggc agc att cgg gtt ctc aag aag ttc act gag aaa tcc      502
Thr Glu Gly Gly Ser Ile Arg Val Leu Lys Lys Phe Thr Glu Lys Ser
        115                 120                 125 aag ctt ctt caa ggc att gag aat ttc cgt ttg gcc atc tta gaa gct      550
Lys Leu Leu Gln Gly Ile Glu Asn Phe Arg Leu Ala Ile Leu Glu Ala
    130                 135                 140 aga gca cac acg ttc gtg tcc cca cgc cac ttt gat tcc gag gtt gtc      598
Arg Ala His Thr Phe Val Ser Pro Arg His Phe Asp Ser Glu Val Val
145                 150                 155                 160 ttg ttc aac att aag ggg aga gcc gta ctt ggg ttg gtg agg gaa agt      646
Leu Phe Asn Ile Lys Gly Arg Ala Val Leu Gly Leu Val Arg Glu Ser
```

-continued

|  | 165 | 170 | 175 |  |
|---|---|---|---|---|
| gaa aca gaa aaa atc acc cta gaa cct gga gac atg ata cac ata cca | | | | 694 |
| Glu Thr Glu Lys Ile Thr Leu Glu Pro Gly Asp Met Ile His Ile Pro | | | | |
|  | 180 | 185 | 190 | | gca ggc aca cca ctg tac atc gtt aac aga gat gag aat gag aag ctc  742
Ala Gly Thr Pro Leu Tyr Ile Val Asn Arg Asp Glu Asn Glu Lys Leu
            195                 200                 205 ctc ctt gcc atg ctc cat ata cct gtc tct act cct gga aaa ttt gag  790
Leu Leu Ala Met Leu His Ile Pro Val Ser Thr Pro Gly Lys Phe Glu
        210                 215                 220 gaa ttt ttc ggg cct gga gga cga gac cca gaa tcg gtc ctc tca gca  838
Glu Phe Phe Gly Pro Gly Gly Arg Asp Pro Glu Ser Val Leu Ser Ala
225                 230                 235                 240 ttc agc tgg aat gtg ctg caa gct gcg ctc caa acc cca aaa gga aag  886
Phe Ser Trp Asn Val Leu Gln Ala Ala Leu Gln Thr Pro Lys Gly Lys
                245                 250                 255 tta gaa agg ctt ttt aat caa cag aac gag gga agt att ttc aaa ata  934
Leu Glu Arg Leu Phe Asn Gln Gln Asn Glu Gly Ser Ile Phe Lys Ile
            260                 265                 270 agc aga gaa cgg gtg cgt gcg ttg gcc ccc acc aag aaa agc tct tgg  982
Ser Arg Glu Arg Val Arg Ala Leu Ala Pro Thr Lys Lys Ser Ser Trp
        275                 280                 285 tgg cca ttc ggc ggc gaa tcc aag gct caa ttc aat att ttc agc aag 1030
Trp Pro Phe Gly Gly Glu Ser Lys Ala Gln Phe Asn Ile Phe Ser Lys
    290                 295                 300 cgt ccc act ttc tcc aac gga tat ggc cgt tta act gaa gtt ggt cct 1078
Arg Pro Thr Phe Ser Asn Gly Tyr Gly Arg Leu Thr Glu Val Gly Pro
305                 310                 315                 320 gat gat gaa aag agt tgg ctt caa aga ctc aac ctc atg ctt acc ttt 1126
Asp Asp Glu Lys Ser Trp Leu Gln Arg Leu Asn Leu Met Leu Thr Phe
                325                 330                 335 acc aac atc acc cag aga tct atg agt act att cac tac aac tca cat 1174
Thr Asn Ile Thr Gln Arg Ser Met Ser Thr Ile His Tyr Asn Ser His
            340                 345                 350 gca acg aag ata gca ctg gtg atg gat ggt aga ggg cat ctt caa ata 1222
Ala Thr Lys Ile Ala Leu Val Met Asp Gly Arg Gly His Leu Gln Ile
        355                 360                 365 tca tgt cca cac atg tca tca agg tca gac tca aag cat gat aag agt 1270
Ser Cys Pro His Met Ser Ser Arg Ser Asp Ser Lys His Asp Lys Ser
    370                 375                 380 agc ccc tca tac cat aga atc agt gcg gac ttg aag cct gga atg gtg 1318
Ser Pro Ser Tyr His Arg Ile Ser Ala Asp Leu Lys Pro Gly Met Val
385                 390                 395                 400 ttt gtt gtc cct cct ggt cat ccc ttc gtc act ata gct tcc aat aaa 1366
Phe Val Val Pro Pro Gly His Pro Phe Val Thr Ile Ala Ser Asn Lys
                405                 410                 415 gag aat ctc ctc ata att tgc ttc gag gtt aac gtt cga gac aac aag 1414
Glu Asn Leu Leu Ile Ile Cys Phe Glu Val Asn Val Arg Asp Asn Lys
            420                 425                 430 aag ttt acg ttt gca ggg aag gac aac att gtg agc tct ctg gac aac 1462
Lys Phe Thr Phe Ala Gly Lys Asp Asn Ile Val Ser Ser Leu Asp Asn
        435                 440                 445 gta gct aag gag ctg gcc ttt aac tat cct tct gag atg gtg aac gga 1510
Val Ala Lys Glu Leu Ala Phe Asn Tyr Pro Ser Glu Met Val Asn Gly
    450                 455                 460 gtc tcc gaa aga aag gag agt ctc ttt ttc ccc ttc gag ttg ccg agc 1558
Val Ser Glu Arg Lys Glu Ser Leu Phe Phe Pro Phe Glu Leu Pro Ser
465                 470                 475                 480 gag gag cgt ggt cgt cgc gct gtt gcg tga gaagcagtgt ggaggtggct   1608

Glu Glu Arg Gly Arg Arg Ala Val Ala
         485                 490

| | |
|---|---|
| gataacgggg aatgtattta gctttgagag tctttaaatt ttctgtattt gttgtaatgt | 1668 |
| tagtagttcc ttaaattggc cagatggagt ttatgtgttt gtaaatgcag ggatgctaac | 1728 |
| ggaataaaat ggccacttgt attgctaaag aaaaaaacca gcccgggccg tcgaccacgc | 1788 |
| gtgccctata gtgagtcgta ttacaatcga attcctgcag cccgggggat ccactagttc | 1848 |
| tagagcggcc gccaccgcgg tggagctcca gcttttgttc cctttagtga gggttaattt | 1908 |
| cgagcttggc gtaatc | 1924 |

<210> SEQ ID NO 6
<211> LENGTH: 3718
<212> TYPE: DNA
<213> ORGANISM: Glycine max

<400> SEQUENCE: 6

| | |
|---|---|
| ttgtaaacga cggccagtga attgtaatac gactcactat agggcgaatt gggtaccggg | 60 |
| ccccccctcg aggtcgacgg tatcgataag cttgattgta atacgactca ctatagggca | 120 |
| cgcgtggtcg acggcccggg ctggtctgag aaactcatta ggcactggaa aattctcaaa | 180 |
| ggaaataatg tgagtcagcc aattcaaacc caccatatct ttattaattt cactttttc | 240 |
| tttatttat aattttagt ctcacagtca cacattttaa caggttatga taacaagggg | 300 |
| caaagataag ggtgagaccg ggattataaa gcgtgtcatt cgctctcaaa atcgtgtcat | 360 |
| tgtagagagt aaaaacctgg tgagagatat tatcatcaca atttggtcct tctgttttc | 420 |
| taatgcccta tcttccttag attatgtttt caattccact gtcaatgtgt cttgcatcag | 480 |
| aatattaatc aattgtgaca ttgagcatgt gattgtgtaa attttcctga taggtttctc | 540 |
| actccaatgc cttttgtcat cctctttata ggtaaagaag catataaagc aagggcaagg | 600 |
| tcatgaaggg ggcatcttta cagtggaagc cccactgcat gcctccaatg tgcaagttct | 660 |
| tgacccagtg acagggtatg tcattgttca gatattgaac tggtgattgc atctccaaac | 720 |
| gggataacat cattaacatg tatgaaagta agagttacca acttttactt gtgcagcaag | 780 |
| ccttgcaagg ttggagttaa atatcttgaa gatggtacta agtcagagt gtccagagga | 840 |
| ataggaacct cagggtccat agtccctcgt cctgagattt aaagataag aactacccca | 900 |
| agacctgcag tccgtaagta tctaacaagc ttaattatgc ttttttcatgt atgagttgtt | 960 |
| gacaaaacat ggccagagcc aatagagaat cgagaaaaag tgagacggaa atgaacttg | 1020 |
| aattatgaga aggtgtgtg aaacaaacaa gccaataatg tggcttatat aatatataat | 1080 |
| atatagatat agaccagagt gagtaacgaa tcactaacta attacatgtg tatatctacc | 1140 |
| taattagatg actcatcaaa caaagcgaac tattgtgata gagactttat ttttcgcaat | 1200 |
| taattcaaag atgtactgct tatcttcttt gctacatgtc tgttgacatg cattgttatc | 1260 |
| cataaccttg ttattatact tggtgttgag aaaggagagt ctccttgcac tttagagaca | 1320 |
| ttctttaaac tgacttgacc ttattgaaaa ttcgagatag caacttagca ccacaccta | 1380 |
| aaaagaaaga tttttagag ggtagattaa ttgttgaata atgttaatca tcaaaggttt | 1440 |
| aagatttatt aagtgctttc cattgtctta aaaatcttgc ttctaggact aggatgtgta | 1500 |
| ttgttacatg atttcccccc cttggtatca actaaagcat gttggacttg cgctccatat | 1560 |
| gcagaaactc aaattaaaaa catcatttgt aatgtatagt aagtgtatat ataacattgt | 1620 |
| aagttgtcga tcaaagttat ttggattaat ggatttaagt cttctataat attccattga | 1680 |

-continued

```
gagccagaag ccaggtccaa aggaataagt aactcgcatg aattcattct cttgcttcta      1740
tacagctatt tttccatctt agtgttgcgg gaaactactt cagttctcgc agatgtgcaa      1800
aacttgtagg gatccatgta gttcagtgaa acccatgctt tcttaattga cagagataca      1860
ttaaaacttt ttacagaatt gagaaaccca agccttgtta attctcaaag atacatttaa      1920
acttttttca gaaacgtgct gagtatttta tcctgtttgt tattcatttt tggcagttgg      1980
tcctaaaaat actcctatga atcttgtgct agagaagact tgcaatgcta aaacaggacg      2040
gggcatgcct gaactttaag gagacgttgc cttgttccga ttaggtaatt gctatcgtga      2100
tgaacaaaaa tttggtgtga atttatcccc ttgccctttg ccatgattca attaaagacg      2160
tgtttggaac acattctaa caccacttta tgatgggtta gacgcaaaat ctagattggg       2220
tagtgtttac acacagttac aaacacattc cttgtttaat gttatcatgc ctaggagttg      2280
aataacttgt aactttacca attagacatt actactagca ttcttttttcc tattcaagtt     2340
gatgttatct ccagttagtg atggtcattt cattccataa acttcaattg ttaaaatgag      2400
tgaaaaggga aaaaggaacc cgtttgattg ttatggttct agtgattttt attaattggg      2460
tttgtccatt agtgtcgatt tgagctaaat agttccccc ccccaaaaga tcagtcttct       2520
cacatgtcat attcatgcgc tggtacccttt ttcatccagt tccaacaaac ttgctgtacg     2580
aagtcaggtt gcatgaaaat agtcaaattt tctttaaggg ggatattata cgtaaataaa      2640
taacgtaacc caaagtgctt acttgttggg taacgtgggt tttggtgttt gatggaccta     2700
gaacactgtt tgttgctctt tatgcttac aaagtaaaaa tggttatcac atttggggaa       2760
aaaatgtagg cccacttatg atatttcgac ctaaatgcaa aatggtttat caatttttttt    2820
atacttagta tgataaaact cctttttttt ttccactggc atactatttc tctaagactt     2880
tttaatagtt ccgataattc ttagcttaaa gaaatacgac aaggttagga atatttttttt    2940
attatgtgac attattttttt aaatattttg cttcatatga atttatacaa tcattataat    3000
ttgacctttt aaatgacttt taaaaatgat cagacctaaa atttgagtct tctgattgag     3060
atgcaaactt atttcttttt atatttttata ttttatactc atttgtttct ctttctatta    3120
tatttctttt ttttcttctc tttatgcaaa aacgtatgac gttgattggt gtctttggca     3180
atcttttttat gacgctcaaa agtgaaaata atatattgttc actttcacct cacgctggcc   3240
ttccgctgat ggtggttgta cgcacttatt tgatttttttt ttcttccaca tttaatgagg    3300
tgaatcagtt agagaaatat taaaaaaaat aaataaataa aggaagacga ctaatacaat     3360
aaagaatacg aaactcacaa tgaatagacc caattagaac catttatttt ccttacaaat     3420
taaagaaaac gttttttttaa caatatatca cattatcatc tattatatttt ttatttatat   3480
tttttataac tttctctatc taggtgtaga ttgacatgag tatacgcacg cacacccagc     3540
tctacttagc agcaattacc cgttttactt gctacttaag agacacgtac attaacactt     3600
gtccttgtgc atgcaattgc caccacattc ctcactccac cctttttcttt atatataaac   3660
aaacacaatg gatcatctca aaccaagagt gagtttgttg ttcctcactg acctcacc       3718
```

<210> SEQ ID NO 7
<211> LENGTH: 4526
<212> TYPE: DNA
<213> ORGANISM: Glycine max

<400> SEQUENCE: 7

```
ttgtaaaacg acggccagtg aattgtaata cgactcacta tagggcgaat tgggtaccgg      60
gccccccctc gaggtcgacg gtatcgataa gcttgattac tatagggcac gcgtggtcga     120
```

```
cggcccgggc tggtactttt gactccctaa ttgacaacta ctgcattgta tcgatattaa      180
tatggaattt ggaatcatgg tccatgcttc atgtattgtg tacctcatat tcaacagcta      240
gtgaacacaa atcttacat acttttgtat ttctatcagt ttataccttc ccaaataaat       300
ggcttatatt gcattgagtt acatattatt gtttagttgg attgtaattt acgagtagtt      360
tgtcacgact gaagaaatta ataaggtata agacacgtcc tgctcccgcg aaattcattt      420
tctgtttatt ctctgtctct gtctctattc aattcaacct tccatttgtt ttcgccagca      480
tccagatttg tgctttctct atcatttcat ttaattaatg tgatgtatgt atggctgaat      540
aaaagatgga ttcctctttt tgtgggggtg gaagcttaat ctatggggct agataaaaaa      600
attcatctgt ttgttgcaca gaataaaata taaattaata attaattaaa cttcaaacat      660
ggacagggca cctccaagtt attttaaaac cgaccatggc cattttttgct ttctgttggt     720 gttcttggct cagcttttgt aattttagac tgcagaaaca tcctgtatgg gttggaaagc      780
agctgagaaa ctcattaggc gctggaaaat tctaagaggg gataatgtat gtgagtcaat      840
tcaaacccac catatgtttg tctctgtgct ctttattaat ttcactttt tatttttataa      900 ttttagtctc acagtcacag agtcacttat gtattcatct aacaggttat gataacaagg      960
ggcaaagata agggtgagac cggattata aagcgtgtca tttgctctca aaatcgtgtc     1020
attgtagagg gtaaaaatct ggtgagatat tataatcact atttggtcct tctgttttttc    1080 taatgcccta tcttctgtag cttttgtttt caattccact gtcagtgtgt cttgcatcag     1140
aatattaatc ggttgtcagt gacattgagc atttaattgt gtaaattttc ctgttagatt     1200
tctcactcca atgccttttg ccgtcctctt tataggtaaa gaagcatatc aagcaagggc     1260
aaggtcataa agggggaatc tttacagtgg aagccccact gcatgcctcc aatgtgcaag     1320
ttcttgaccc agtgacaggg tatgtacatg ttagatattg aactggtgat tgcttctcca     1380
aatgggataa catgtatgta agtaagagta acctactttt acttgtgcag caagccttgc     1440
aaggttagag ttaaaatatc ttgaagatgg tactaaagtc agagtgtcca gaggaatagg     1500
agcatcaggg ttcatagtcc ctcgtcccaa gatcttaaag ataagaacta ccccaagacc     1560
tacagtccgt aagtatctaa caagcttatg ttttttcctt gtatgagttg ttgataaaac     1620
atggccagag ccaatagaga attgagaaaa ggtgagaaac agaaaatgaa cttgaattat     1680
gagaaaggtg tgggaaacaa acaagccaat aatgtggctt atataatata tagatataga     1740
ctagagtgag taacgaatca ctaactaatt acatgtgcat atctacctaa ttagatgatt     1800
cgtcaaacga agcaaagtat tgtgatagat agttgatttt tctcaaataa ttctaagatg     1860
taatacttat attctttgct acatgtctgt tgacatacat tgttatccat aaccttgtta     1920
ttatacttgg tgttaaaaaa ggagagtctc cttgcacttt agagacattc tttaaactga     1980
cttgacctta ttgaaataca taattctagt taccaactta gcaccacacc ataaaaggaa     2040
agatttttaa acggtagatt gattgttgaa taatgttaat catcaaaggt ttaagattta     2100
ttaagtgctt tccattgtct taaaatattg cttctaggac taggatgtgt atattggtta     2160
catgatttcc ccgccttcgt atcaacttaa gcatgttgga cttgcaccca tgcagaaaa      2220 ctcaaataaa aaacttcatt tgtaaggtat aataagtgta tatataacat tgtaagttgt     2280
caatcagagt aatttggatt gatggatatt taagtcttct ataatatttc atttagagcc     2340
agaagccagg ttcaaaggaa taggtaattc acatgaattc attctcttgt ttctatacag     2400
ttattatttt ttccatctta gtgttgcagg aaactacctc agttgttgta gatgtgcaaa     2460
```

```
acttgtatgg atatatatac tgttcagtgt tgggaaaccc atgctttctt aattcacaga    2520
gatacattta aacttttttt agaaacttgc ttagtatctt atcctgttat tcattttttgg   2580 cagttggtcc taaagatact cctatgaatc ttgtgctaga aagacttac gatgctaaaa     2640 caggacgggg catgcctgaa ctttaaggag acgttgccct gttccacttc caattaggta    2700
actgctatcg tgatgaacaa aaatttggtg tgagtttatc accttgtcct ttgccatgat    2760
tcaattaaaa gcgtgtttgg actttggaac ctcattctaa caccaccta tgatgggtta     2820 gacgcaaaat ctagactggg tagtgtttaa cgtgtatctg tgtgaacaca gttacaaacg    2880
cattccatgt ttaatgctac catgcctagg agttgaatca tttgtaactt taccaattta    2940
gtcattacta ctagcattct tttccctatt caagttgatg ttagctccag ttagggatgg    3000
tcatttcact ccataaactt taattgttag gtgagtggaa gaggaacccg tttgattgtt    3060
atggttctag ttctagtgat tttttattaat tgggttcgac catattagtg tttgatttga   3120
gctatagata gttttttccc caaaagatca gttttctcac atgtcagatt catgggttgg    3180
tactcttttc atccagttcc aacaaacttg ctgttcgaac tacgaagtca gtcttactta    3240
ttgggtaaca tgtgggtttt ggtgtttaat ggatctagaa tactgtttgt agctaaacct    3300
atcttatcat atagggccta aaaagtaaaa ttggttatta catttggaaa aaaagaaata    3360
atctaggccc actggcacac tgaaaaacgt tttcaatgaa taatttaata gttttttttt    3420
tataaaaaaa ttttaataaa aataatgga gttttttaaaa atattacaac aatctgtttc    3480
tctaaggttt tttaatagtt cagataattc atagcttaga gcaatacgac atggttagga    3540
agcataaaaa aaatatacga catggttagg aattttttttt tagtatgtct gacataattt    3600
tttaaatgtt ttggcttcat atgaatttaa cagtgcgtca tatgaactta cacactcatt    3660 atattttta acctttttaaa tgattttttaa aaaatatgac agatgcaatc ttattctcac    3720 ttttatact ttcactactg cttcatatga cctaaagtca gagaaatatt ttaaaaagat    3780
aaatacgata aagaatacga tgagaaagaa acctcacaca atgaatagac caaattagac   3840
ctatttattt tccttagaaa taagaaaat aattattttt tatttttttca cattacattt     3900 atattttct atcactttct ctatttaggt attgattgac atatgagtgt acatgaactt    3960
tttttaaaaa aaaagcgtaa atattaatta tattcatgca tttgttttct gtctttcatt    4020
ttctatttaa tcttacgtta tcaataatct attattaaat tttatagttg atgatgaata    4080
tataagagat ataaataaaa aataattaa ttttataata aaaattaaaa ataattaat      4140 tatttttgaga taaattttttt ttaagagaac aattataaac ggagagtatt atatttagtt  4200
ttatgtgtac cgggtacgtg tctactaaca tggtgtctct ccatcatttt cgtaggaaaa    4260
aacattatag gagtatgaaa aaagcaaaag ttttgtctgt ttatggtttt gtatataccc    4320
agctctactt ggcagcaatt acccgtcttg cttgctactt acgagacacg tacattaaca    4380
cttgtcctag ctagtgcatg caattgccac cccattcctc actcctccct tttccttctc    4440
tttatattta tatatataaa taaacaaaca caatgcatca tctcaaagaa attaagagag    4500 ttttttttgtt cctcactgac caagcc                                         4526
```

<210> SEQ ID NO 8
<211> LENGTH: 23
<212> TYPE: DNA
<213> ORGANISM: Artificial Sequence
<220> FEATURE:
<223> OTHER INFORMATION: Description of Artificial Sequence:
      Oligonucleotide used to amplify a region of the
      SBP2 cDNA or 5' regulatory region.

-continued

<400> SEQUENCE: 8
tgtaaaacga cggccagtga att    23

<210> SEQ ID NO 9
<211> LENGTH: 23
<212> TYPE: DNA
<213> ORGANISM: Artificial Sequence
<220> FEATURE:
<223> OTHER INFORMATION: Description of Artificial Sequence:
      Oligonucleotide used to amplify a region of the
      SBP2 cDNA or 5' regulatory region.

<400> SEQUENCE: 9
gattacgcca agctcgaaat taa    23

<210> SEQ ID NO 10
<211> LENGTH: 27
<212> TYPE: DNA
<213> ORGANISM: Artificial Sequence
<220> FEATURE:
<223> OTHER INFORMATION: Description of Artificial Sequence:
      Oligonucleotide used to amplify a region of the
      SBP2 cDNA or 5' regulatory region.

<400> SEQUENCE: 10
atggcgacca gagccaagct ttcttta    27

<210> SEQ ID NO 11
<211> LENGTH: 27
<212> TYPE: DNA
<213> ORGANISM: Artificial Sequence
<220> FEATURE:
<223> OTHER INFORMATION: Description of Artificial Sequence:
      Oligonucleotide used to amplify a region of the
      SBP2 cDNA or 5' regulatory region.

<400> SEQUENCE: 11
cgcaacagcg cgacgaccac gctcgct    27

<210> SEQ ID NO 12
<211> LENGTH: 27
<212> TYPE: DNA
<213> ORGANISM: Artificial Sequence
<220> FEATURE:
<223> OTHER INFORMATION: Description of Artificial Sequence:
      Oligonucleotide used to amplify a region of the
      SBP2 cDNA or 5' regulatory region.

<400> SEQUENCE: 12
atggcgacca gagccaagct ttcttta    27

<210> SEQ ID NO 13
<211> LENGTH: 27
<212> TYPE: DNA
<213> ORGANISM: Artificial Sequence
<220> FEATURE:
<223> OTHER INFORMATION: Description of Artificial Sequence:
      Oligonucleotide used to amplify a region of the
      SBP2 cDNA or 5' regulatory region.

<400> SEQUENCE: 13
gaagggatga ccaggaggga caacaaa    27

<210> SEQ ID NO 14
<211> LENGTH: 23
<212> TYPE: DNA

```
<213> ORGANISM: Artificial Sequence
<220> FEATURE:
<223> OTHER INFORMATION: Description of Artificial Sequence:
      Oligonucleotide used to amplify a region of the
      SBP2 cDNA or 5' regulatory region.

<400> SEQUENCE: 14
ttgtaaacga cggccagtga att                                          23

<210> SEQ ID NO 15
<211> LENGTH: 23
<212> TYPE: DNA
<213> ORGANISM: Artificial Sequence
<220> FEATURE:
<223> OTHER INFORMATION: Description of Artificial Sequence:
      Oligonucleotide used to amplify a region of the
      SBP2 cDNA or 5' regulatory region.

<400> SEQUENCE: 15
ggtgaggtca gtgaggaaca aca                                          23
```

NUCLEIC ACIDS ENCODING SUCROSE-BINDING PROTEINS

CROSS REFERENCE TO RELATED APPLICATIONS

This application is a §371 U.S. National Stage application of International Application No. PCT/US98/10465, filed May 21, 1998 (published in English under PCT Article 21(2), which in turn claims the benefit of U.S. Provisional Application No. 60/047,568, filed May 22, 1997.

GOVERNMENTAL SUPPORT

This invention was made with government support under grant number IBN-9514410, awarded by the National Science foundation. The government has certain rights in the invention.

FIELD OF THE INVENTION

This invention relates to carbohydrate metabolism in plants, and in particular to sucrose-binding proteins (SBPs). Aspects of the invention include a novel SBP gene isolated from soybean, and modified SBPs having enhanced sucrose uptake activity. Nucleic acid vectors, transgenic cells and transgenic plants having modified sucrose uptake activity are also provided. The invention also relates to promoter sequences useful for controlling expression of transgenes in plants, including SBP transgenes.

BACKGROUND OF THE INVENTION

The regulation of sucrose transport in plants has a major impact on plant growth and productivity. Through photosynthesis, plants fix atmospheric carbon dioxide into triose phosphates, which are then used to produce sucrose and other carbohydrates. These carbohydrates are then transported throughout the plant for use as energy sources, carbon skeletons for biosynthesis and storage for future growth needs. Sucrose is the major form of transported carbohydrate. The ability of plant cells actively to transport sucrose across the plasma membrane so that the sucrose that is mobilized in the phloem can be taken into cells for use is a critical step in sucrose utilization.

The development of plant seeds involves the accumulation of carbon and nitrogen reserves in forms that can both withstand desiccation and be utilized as an energy source by the developing embryo during germination. The accumulation of carbon in developing seeds is mediated by specific plasma membrane proteins (Overvoorde et al., 1996; Riesmeier et al., 1992; Bush, 1993). Photoaffinity labeling of membranes isolated from soybean cotyledon tissue with a photolyzable sucrose analog identified a distinct 62 kD sucrose-binding protein, or SBP (Ripp et al., 1988). Analysis of the cDNA encoding the SBP and its deduced amino acid sequence indicates that the SBP contains a single hydrophobic domain at its N-terminus but otherwise is a hydrophilic protein lacking the expected membrane-spanning hydrophobic segments typically present in transport proteins (Grimes et al., 1992). Biochemical analysis of the topology of the SBP demonstrates that it is tightly associated with the external leaflet of the plasma membrane (Overvorrde & Grimes, 1994). The involvement of the SBP in sucrose uptake was implicated by immunolocalization experiments demonstrating that the SBP is exclusively associated with the plasma membrane of cells involved in active sucrose uptake (Grimes et al., 1992). Kinetic analysis of SBPmediated sucrose uptake in a yeast system indicates that the uptake is specific for sucrose but is proton independent and relatively nonsaturable, thus defining a novel mechanism for sucrose uptake (Overvoorde et al., 1996).

Sucrose uptake in developing seeds affects two significant agricultural characteristics of the mature seed: the carbohydrate content of the resulting seed grain, and the vitality of the seedling that emerges when the seed grain is planted. Enhanced sucrose uptake activity in developing seeds may be desirable where it is an advantage to increase the carbohydrate content of the seed (e.g., where the seed is the primary plant material harvested, such as soybean). In contrast, decreased sucrose uptake activity in seeds might be desirable where the vegetative material of the plant is harvested. Thus, plants having modified sucrose uptake activity during seed development would be of significant agricultural importance, and it is to such plants that the present invention is directed.

SUMMARY OF THE INVENTION

The present invention provides isolated nucleic acid molecules encoding plant sucrose binding proteins, which are key proteins in the uptake of sucrose into developing seeds. In one embodiment, the invention provides modified forms of sucrose binding proteins that are shown to have enhanced sucrose uptake activity.

The previously described sucrose binding protein from soybean (Overvoode et al., 1996) is herein referred to as SBP1. A new SBP is provided herein and is referred to as SBP2. The SBP2 polypeptide is shown to be 489 amino acid residues in length, and to be expressed at enhanced levels during seed development. The SBP2 polypeptide is shown to have sucrose uptake activity in a heterologous yeast assay system.

In addition, modified forms of the SBP1 and SBP2 proteins are provided having enhanced sucrose uptake activity. In one embodiment, such forms are deletion mutants in which amino acid residues are removed from the C-terminus of the proteins. By way of example, removal of 80 amino acid residues from the C-terminus of the SBP1 protein is shown to produce increased sucrose uptake in the yeast assay system.

The invention also provides 5' regulatory regions (including promoter sequences) of the soybean SBP1 and SBP2 genes. These regulatory regions confer specific or enhanced expression in developing seeds and so may be used to express any transgene in developing seeds.

Thus, in one aspect, the invention provides a modified plant sucrose binding protein wherein the modified sucrose binding protein has a modified amino acid sequence compared to a corresponding wild-type sucrose binding protein, and wherein expression of the modified sucrose binding protein in a yeast assay system confers enhanced sucrose uptake compared to the corresponding wild-type sucrose binding protein. In particular embodiments, modified sucrose binding proteins provided by the invention enhance sucrose uptake in the yeast assay system by at least 10%, and preferably by at least 25%, compared to the wild-type sucrose binding protein. In certain embodiments, the modified plant sucrose binding proteins have a modified amino acid sequence comprising a C-terminal truncation compared to the wild-type sucrose binding protein. Such a truncation is typically of between about 10 and about 100 amino acids, and is preferably of about 80 amino acids. Although such modified SBPs may be produced from any known sucrose binding proteins, modified forms of SBP1 and SBP2 are exemplary of the invention. Modified forms of SBP1 and SBP2 include those forms having the amino acid sequences shown in Seq. I.D. Nos. 2 and 4, respectively.

In another aspect of the invention, nucleic acid molecules encoding modified plant sucrose binding proteins are provided, together with vectors comprising such nucleic acid molecules. The invention also provides transgenic plants expressing modified sucrose binding proteins. Such transgenic plants may have modified sucrose uptake activity, particularly in developing seeds.

In another aspect, the invention provides an isolated nucleic acid molecule encoding a SBP2 sucrose binding protein or a variant of a SBP2 protein. Such proteins may comprise an amino acid sequence as shown in Seq. I.D. Nos. 3 and 4, or sequences having at least 70% and preferably at least 90% sequence identity with these sequences. Recombinant expression cassettes comprising such nucleic acid molecules are also provided by the invention, as are transgenic plants comprising such recombinant expression cassettes.

Another aspect of the invention is a recombinant nucleic acid molecule comprising a promoter sequence operably linked to a nucleic acid sequence, wherein the promoter sequence comprises a SBP1 or SBP2 promoter. Such promoters preferably comprise at least 25 consecutive nucleotides of the 5' regulatory sequences shown in Seq. I.D. Nos. 6 and 7. In particular embodiments, the nucleic acid sequence comprises a plant sucrose binding protein. Transgenic plants comprising such recombinant nucleic acid molecules are also an aspect of the invention.

These and other aspects of the invention are discussed in more detail in the following description.

BRIEF DESCRIPTION OF THE DRAWINGS

FIGS. 1a–1b show an alignment of the SBP1 and SBP2 protein sequences.

SEQUENCE LISTING

Figure 2:
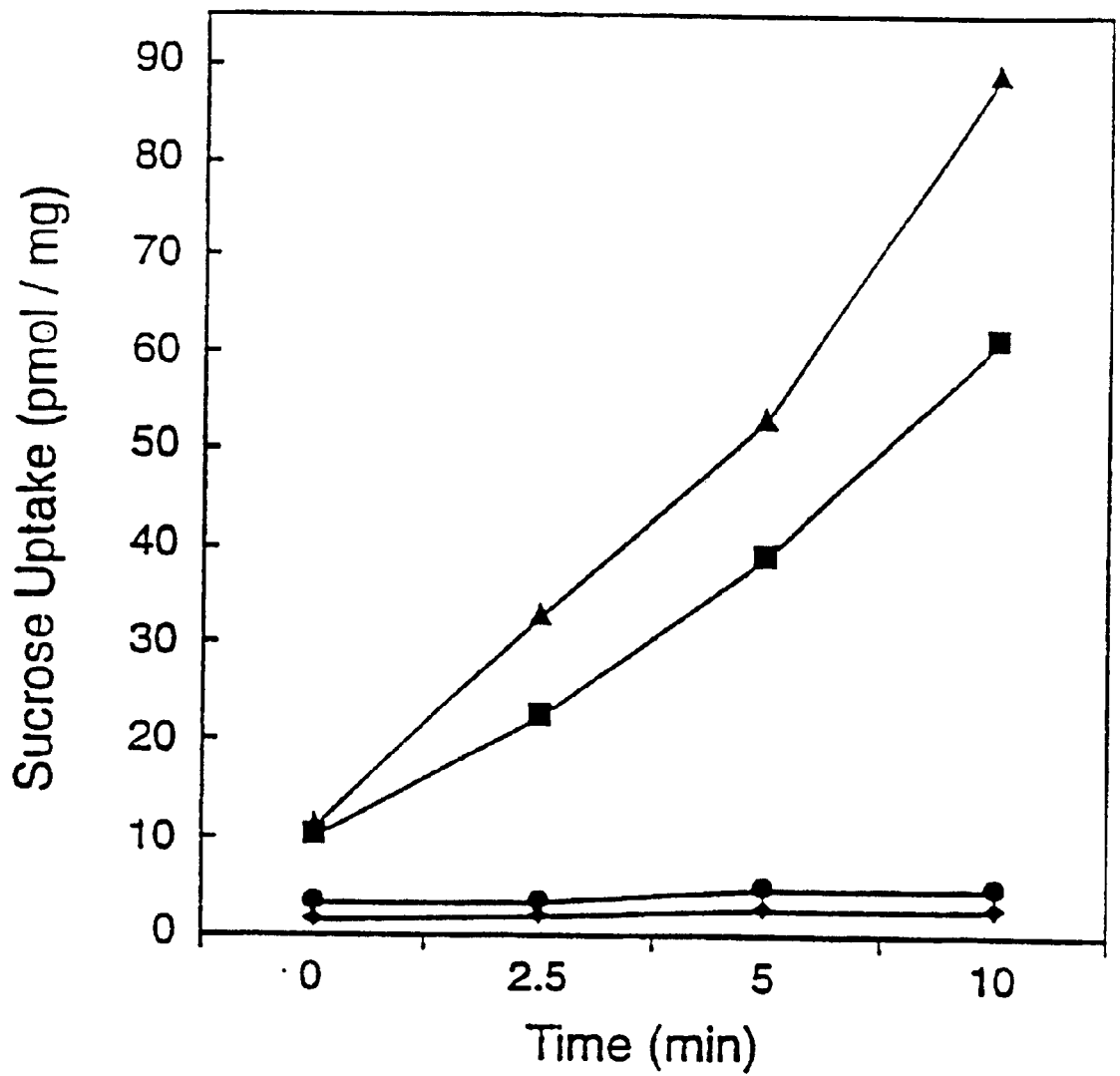
FIG. 2 is a graph showing sucrose uptake activity in the yeast assay system.

The nucleic and amino acid sequences listed in the sequence listing are shown using standard single-letter abbreviations for nucleotide bases, and three-letter code for amino acids. Only one strand of each nucleic acid sequence is shown, but the complementary strand is understood to be included by any reference to the displayed strand.

Seq. I.D. No. 1 shows the amino acid sequence of the SBP1 protein.

Seq. I.D. No. 2 shows the amino acid sequence of the truncated SBP1 protein from which the C-terminus 80 amino acids are deleted.

Seq. I.D. No. 3 shows the amino acid sequence of the SBP2 protein.

Seq. I.D. No. 4 shows the amino acid sequence of the truncated SBP2 protein from which the C-terminus 80 amino acids are deleted.

Seq. I.D. No. 5 shows the SBP2 cDNA sequence.

Seq. I.D. No. 6 shows the SBP2 gene 5' regulatory region.

Seq. I.D. No. 7 shows the SBP1 gene 5' regulatory region.

Seq. I.D. Nos. 8–14 show oligonucleotides that may be used to amplify various regions of the SBP2 cDNA or 5' regulatory region.

DETAILED DESCRIPTION OF THE INVENTION

I. Methods

Standard molecular biology methods may be used to practice the present invention. Such methods are described in many publications, including Sambrook et al., (1989), Ausubel et al. (1994), Innis et al. (1990), Weissbach & Weissbach (1989), Tijssen (1993).

II. Definitions

Unless otherwise noted, technical terms are used according to conventional usage. Definitions of common terms in molecular biology may be found in Benjamin Lewin, Genes V published by Oxford University Press, 1994 (ISBN 0-19-854287-9); Kendrew et al (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference,* published by VCH Publishers, Inc., 1995 (ISBN 1-56081-569-8). The nomenclature for DNA bases as set forth at 37 CFR §1.822 and the standard three letter codes for amino acid residues are used herein.

In order to facilitate review of the various embodiments of the invention, the following definitions of terms is provided:

Sucrose binding protein (SBP) SBPs are involved in sucrose uptake in plants. This activity can be conveniently determined and measured using the yeast sucrose uptake assay originally described by Overvoorde et al. (1996), which is also described in detail below; in this assay system, SBPs confer sucrose uptake ability on yeast cells that are otherwise unable to take up sucrose. Use of the term SBP refers generally to any sucrose binding protein, including the sucrose binding protein previously described by Grimes et al. (1992). This invention provides a cDNA encoding a previously unreported sucrose binding protein, the SBP2 protein from soybean (Glycine max). However the invention is not limited to this particular SBP: other nucleotide sequences which encode SBP enzymes are also part of the invention, including variants on the disclosed Glycine gene sequences and orthologous sequences from other plant species, the cloning of which is now enabled. Such sequences share the essential functional characteristic of encoding an enzyme that is capable of mediating sucrose uptake in the described yeast assay system. Nucleic acid sequences that encode SBPs and the proteins encoded by such nucleic acids share not only this functional characteristic, but also a specified level of sequence similarity (or sequence identity), as addressed below. The concept of sequence identity can also be expressed in the ability of two sequences to hybridize to each other under stringent conditions.

The present invention also provides modified SBPs having altered functional characteristics, as well as nucleic acid sequences encoding such proteins. An SBP isolated from an untransformed (wild-type) plant may be referred to as having a wild-type amino acid sequence. Modified SBPs have amino acid sequences that differ from the wild-type amino acid sequence. Such differences may take the form of amino acid deletions, additions, substitutions or truncations. A protein having amino acid deletions lacks one or more of the amino acid residues present in the wild-type sequence; such residues may be deleted from any portion of the protein. In contrast, a truncated protein is one in which one or more amino acids are deleted from the N and/or C terminus of the protein. Thus, truncated proteins are a sub-class of proteins having amino acid deletions.

Nucleic acid sequences encoding modified SBPs can readily be produced using standard methodologies, such as site directed mutagenesis and polymerase chain reaction amplification.

Sequence identity: the similarity between two nucleic acid sequences, or two amino acid sequences is expressed in terms of the similarity between the sequences, otherwise referred to as sequence identity. Sequence identity is frequently measured in terms of percentage identity (or similarity or homology); the higher the percentage, the more similar the two sequences are.

The calculation of percentage of sequence identity for amino acid sequences may take into account conservative amino acid substitutions. Conservative amino acid substitutions involve the replacement of one amino acid residue with another residue having similar chemical and biological properties (e.g., charge or hydrophobicity). Such substitutions typically do not change the functional properties of the protein, and should therefore be accounted for in the calculation of sequence identity by assigning a value that is in between values assigned for identity (i.e., no change at that amino acid position) and non-conservative residue changes. Thus, conservative amino acid changes are scored as a partial rather than a full mismatch, thereby increasing the percentage sequence identity. For example, if an identical amino acid is given a score of one and a non-conservative substitution is given a score of zero, a conservative substitution might be given a score of 0.5. The scoring of conservative substitutions is calculated, e.g., according to the algorithm of Meyers and Miller (1988) e.g., as implemented in the program PC/GENE (Intelligenetics, Mountain View, Calif., USA).

Methods of alignment of sequences for comparison are well known in the art. Various programs and alignment algorithms are described in: Smith and Waterman (1981); Needleman and Wunsch (1970); Pearson and Lipman (1988); Higgins and Sharp (1988); Higgins and Sharp (1989); Corpet et al. (1988); Huang et al. (1992); and Pearson et al. (1994). Altschul et al. (1994) presents a detailed consideration of sequence alignment methods and homology calculations.

The NCBI Basic Local Alignment Search Tool (BLAST) (Altschul et al., 1990) is available from several sources, including the National Center for Biological Information (NCBI, Bethesda, Md.) and on the Internet, for use in connection with the sequence analysis programs blastp, blastn, blastx, tblastn and tblastx. It can be accessed at <http://www.ncbi.nlm.nih.gov/BLAST/>. A description of how to determine sequence identity using this program is available at <http://www.ncbi.nlm.nih.gov/BLAST/blast_help.html>.

Homologs of the disclosed SBP2 protein are characterized by possession of at least 80% sequence identity counted over the full length alignment with the disclosed amino acid sequence of the soybean SBP2 amino acid sequence using the NCBI Blast 2.0, gapped blastp set to default parameters. Such homologous peptides will more preferably possess at least 85%, more preferably at least 90% and still more preferably at least 95% sequence identity determined by this method. When less than the entire sequence is being compared for sequence identity, homologs will possess at least 90% and more preferably at least 95% and more preferably still at least 98% sequence identity over short windows of 10–20 amino acids. Methods for determining sequence identity over such short windows are described at <http://www.ncbi.nlm.nih.gov/BLAST/blast_FAQs.html>. Homologs having the sequence identities described above will also possess the ability to mediate sucrose uptake in the described yeast assay system. The present invention provides not only the peptide homologs are described above, but also nucleic acid molecules that encode such homologs.

Homologs of the soybean SBP2 gene are similarly characterized by possession of at least 70% sequence identity counted over the full length alignment with the disclosed Glycine SBP2 gene sequence using the NCBI Blast 2.0, gapped blastn set to default parameters. Such homologous nucleic acids will more preferably possess at least 75%, more preferably at least 80% and still more preferably at least 90% or 95% sequence identity determined by this method. When less than the entire sequence is being compared for sequence identity, homologs will possess at least 85% and more preferably at least 90% and more preferably still at least 95% sequence identity over 30 nucleotide windows. Homologs having the sequence identities described above will, in some embodiments, also encode a polypeptide having ability to mediate sucrose uptake in the described yeast assay system. However, homologs as defined above are useful for modifying sucrose uptake activity in transgenic plants (for example, as used in antisense constructs) even when they do not encode a functional peptide.

Another indication that two nucleic acid molecules are substantially homologous is that the two molecules hybridize to each other under stringent conditions when one molecule is used as a hybridization probe, and the other is present in a biological sample, e.g., genomic material from a cell. Specific hybridization means that the molecules hybridize substantially only to each other and not to other molecules that may be present in the genomic material. Stringent conditions are sequence dependent and are different under different environmental parameters. Generally, stringent conditions are selected to be about 5° C. to 20° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Conditions for nucleic acid hybridization and calculation of stringencies can be found in Sambrook et al. (1989) and Tijssen (1993). Hybridization conditions and stringencies are further discussed below.

Nucleic acid sequences that do not show a high degree of identity may nevertheless encode similar amino acid sequences, due to the degeneracy of the genetic code. It is understood that changes in nucleic acid sequence can be made using this degeneracy to produce multiple nucleic acid sequence that all encode substantially the same protein.

Probes and primers: Nucleic acid probes and primers may readily be prepared based on the nucleic acids provided by this invention. A probe comprises an isolated nucleic acid attached to a detectable label or reporter molecule. Typical labels include radioactive isotopes, ligands, chemiluminescent agents, and enzymes. Methods for labeling and guidance in the choice of labels appropriate for various purposes are discussed, e.g., in Sambrook et. al. (1989) and Ausubel et al. (1987).

Primers are short nucleic acids, preferably DNA oligonucleotides 15 nucleotides or more in length. Primers may be annealed to a complementary target DNA strand by nucleic acid hybridization to form a hybrid between the primer and the target DNA strand, and then extended along the target DNA strand by a DNA polymerase enzyme. Primer pairs can be used for amplification of a nucleic acid sequence, e.g., by the polymerase chain reaction (PCR), or other nucleic-acid amplification methods known in the art.

Methods for preparing and using probes and primers are described, for example, in Sambrook et al. (1989), Ausubel et al. (1987), and Innis et al., (1990). PCR primer pairs can be derived from a known sequence, for example, by using computer programs intended for that purpose such as Primer (Version 0.5, © 1991, Whitehead Institute for Biomedical Research, Cambridge, Mass.). One of skill in the art will appreciate that the specificity of a particular probe or primer increases with its length. Thus, for example, a primer comprising 20 consecutive nucleotides of the SBP1 or SBP2 gene 5' regulatory region will anneal to a target sequence (e.g., a corresponding SBP regulatory region from Faba bean) with a higher specificity than a corresponding primer of only 15 nucleotides. Thus, in order to obtain greater specificity, probes and primers may be selected that comprise 20, 25, 30, 35, 40, 50 or more consecutive nucleotides of the nucleic acid sequences disclosed herein.

Transformed: A transformed cell is a cell into which has been introduced a nucleic acid molecule by molecular biology techniques. As used herein, the term transformation encompasses all techniques by which a nucleic acid molecule might be introduced into such a cell, including Agrobacterium transformation, plasmid transformation, viral transfection and introduction of naked DNA by electroporation, lipofection, and particle gun acceleration.

Vector: A nucleic acid molecule as introduced into a host cell, thereby producing a transformed host cell. A vector may include nucleic acid sequences that permit it to replicate in the host cell, such as an origin of replication. A vector may also include one or more selectable marker genes and other genetic elements known in the art.

Isolated: An "isolated" biological component (such as a nucleic acid or protein) has been substantially separated or purified away from other biological components in the cell of the organism in which the component naturally occurs, i.e., other chromosomal and extrachromosomal DNA and RNA, and proteins. Nucleic acids and proteins which have been "isolated" thus include nucleic acids and proteins purified by standard purification methods. The term also embraces nucleic acids and proteins prepared by recombinant expression in a host cell as well as chemically synthesized nucleic acids.

Purified: The term purified does not require absolute purity; rather, it is intended as a relative term. Thus, for example, a purified SBP preparation is one in which the SBP is more enriched than the protein is in its natural environment within a cell. Preferably, a preparation of SBP is purified such that the SBP represents at least 50% of the total protein content of the preparation.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein coding regions, in the same reading frame.

Recombinant: A recombinant nucleic acid is one that has a sequence that is not naturally occurring or has a sequence that is made by an artificial combination of two otherwise separated segments of sequence. This artificial combination is often accomplished by chemical synthesis or, more commonly, by the artificial manipulation of isolated segments of nucleic acids, e.g., by genetic engineering techniques.

Ortholog: Two nucleotide or amino acid sequences are orthologs of each other if they share a common ancestral sequence and diverged when a species carrying that ancestral sequence split into two species. Orthologous sequences are also homologous sequences.

Transgenic plant: as used herein, this term refers to a plant that contains recombinant genetic material not normally found in plants of this type and which has been introduced into the plant in question (or into progenitors of the plant) by human manipulation. Thus, a plant that is grown from a plant cell into which recombinant DNA is introduced by transformation is a transgenic plant, as are all offspring of that plant which contain the introduced DNA (whether produced sexually or asexually). Transgenic plants may be produced from any transformable plant species, both monocotolydenous and dicotyledenous plants, including but not limited to soybean, rice, wheat, barley, and maize.

III. The SBP2 cDNA and Encoded SBP2 Peptide

The nucleic acid sequence of the SBP2 cDNA is shown in Seq. I.D. No. 5, and the amino acid sequence of the SBP2 protein is shown in Seq. I.D. No. 3. A comparison of the amino acid sequences of SBP1 and SBP2 is shown in FIG. 1.

i. Differential expression of SBP1 and SBP2 genes in soybean leaves and cotyledons.

The sense and antisense RNAs of $^{32}$P-labeled SBP1 and SBP2 5'-flanking region were synthesized in vitro and $5.3 \times 10^5$ cpm of a SBP1 sense, SBP1 antisense, SBP2 sense or SBP2 antisense RNA probe were hybridized with 5 μg poly(A+) mRNA from soybean leaves and cotyledons. SBP1 and SBP2 transcripts were observed to accumulate to similar levels in soybean cotyledons. In contrast, no SBP1 and SBP2 transcripts were detected in 4-wk old soybean leaves.

ii. Differential Expression of Soybean SBP1 and SBP2 genes

The expression patterns of the SBP1 and SBP2 genes were examined in soybean seeds using RNase protection methods. Five stages of seed cotyledon development were used (Stage 1=or <4 mm, Stage 2=5–6 mm, Stage 3=7 mm, Stage 4=9 mm, Stage 5=11–12 mm). During cotyledon development, an SBP1 antisense probe protected three major fragment (119, 111, and 97 nucleotides), indicating that three different transcription start sites were used. The SBP1 mRNA level reaches a plateau at stage 3, and this expression level is maintained until stage 5. In contrast, 5 protected fragments were detected when using SBP2 antisense probe, and SBP2 mRNA level continuously increased until seed size reached 11–12 mm. Quantitative data indicated that SBP1 mRNA level is three time more abundant than that of SBP2. The mRNA level of leaf tip is very low. However, low levels of SBP1 mRNA can be observed in 3 mm leaf tips after prolonged exposure. These data indicate that both SBP1 and SBP2 mRNAs are actively and differentially transcribed during seed development.

IV. 5' Regulatory Regions of SBP1 and SBP2

Given the tissue-specific expression of the SBP1 and SBP2 genes, the regulatory regions of these genes responsible for conferring such expression are of interest, and may be used to regulate transgene expression in a similarly tissue-specific manner.

The 5' regulatory regions of SBP1 and SBP2 are shown in Seq. I.D. Nos. 6 and 7, respectively.

V. Modified SBPs Having Enhanced Sucrose Uptake Activity

The yeast assay system described by Overvoorde et al (1996) was used to determine the effect of modifying the amino acid sequence of the SBP proteins. This assay uses a derivative of the yeast strain susy7 (Riesmeier et al., 1992) which has a spinach sucrose synthase cDNA stably integrated into its genome to mediate the intracellular hydrolysis of sucrose. However, this yeast strain lacks the ability to transport sucrose and so is unable to grow on a medium containing sucrose as the sole carbon source (Riesmeier et al., 1992). To generate a host strain that permits selection for yeast transformed with a sucrose binding protein gene, the susy7 strain was selected for uracil auxotrophy by growth on medium containing 5'-fluoroorotic acid (Overvoorde et al., 1996). The resulting strain, susy7/ura3 is unable to grow on a medium lacking uracil and containing glucose as the sole carbon source.

Chimeric genes consisting of the yeast alcohol dehydrogenase 1 (ADH1) promoter, an SBP open reading frame and the ADH1 polyadenylation signal were constructed in the yeast vector pMK195 as described by Overvoorde et al. (1996) to create plasmids designated pYESBP. The susy7/ura3 yeast strain was transformed with these constructs using a small-scale LiOAc-based procedure essentially as described by Gietz et al. (1992). Transformed yeast were then plated on the uracil dropout selection medium containing 2% glucose (CM[GLU]) or 2% sucrose (CM[SUC]) (Ausubel et al., 1994).

Uptake assays were performed by growing the transformed yeast cells to an $OD_{600}$ of 0.5 to 1.3 in YPD, harvested by centrifugation, washed twice with 25 mM Mes-KOH, pH 5.5, 0.5–2.5 $\mu$Ci of $^{14}C$ sucrose, and unlabeled sucrose at twice the final concentration. Aliquots of the uptake solution and cells were collected at specified time points, and uptake was quenched by transfer to 5 ml of ice-cold water. The cells were collected by filtration through glass fiber filters and washed five times with 5 ml of ice-cold water. The radioactivity taken up by the cells was determined by liquid scintillation counting. All uptake assays were performed in a final concentration of 1 mM sucrose.

Nucleic acid sequences encoding modified forms of the SBP1 protein were constructed and introduced into the pYESBP constructs described above. FIG. 2 shows the sucrose uptake rate obtained with yeast cells transformed with the pMK195 vector only (filed circles), and constructs expressing the full length SBP1 protein (filled square) and a truncated SBP1 protein missing the C-terminal 80 amino acids (filled triangle). The amino acid sequence of this truncated SBP1 protein is shown in Seq. I.D. No. 2. The truncated protein comprises residues 1–444 of the full length SBP1.

This surprising result indicates that enhanced sucrose uptake in plants may be achieved by introducing transgenes encoding modified SBPs. Modified SBPs having enhanced sucrose uptake activity include forms of SBP1 and SBP2 having C-terminal deletions. Such deletions include removal of about 80 amino acids from the C-terminal, but deletions of greater or fewer than 80 amino acids may also be employed. The sucrose uptake activity any particular deletion may readily be determined using the yeast sucrose uptake assay described above. Thus, by way of example, SBP proteins having C-terminal deletions of between 10 and 100 amino acids are candidates for enhanced sucrose uptake activity and may be assayed using this system.

EXAMPLES

The following examples are illustrative of various embodiments of the present invention.

Example One
Preferred Method for Producing SBP Nucleic Acids

This invention provides a SBP2 cDNA sequence and the amino acid sequence of the SBP2 protein, modified SBP proteins having enhanced sucrose uptake activity, and 5' regulatory regions for the SBP1 and SBP2 genes. The polymerase chain reaction (PCR) may now be utilized in a preferred method for producing nucleic acid sequences encoding the various SBP proteins described in the invention, as well as the SBP gene 5' regulatory regions. PCR amplification of cDNAs encoding the SBP proteins of the present invention may be accomplished either by direct PCR from a plant cDNA library or by Reverse-Transcription PCR (RT-PCR) using RNA extracted from plant cells as a template. Amplification of SBP gene sequences and 5' regulatory regions may be accomplished by direct PCR amplification from plant genomic DNA, or from a plant genomic library. Methods and conditions for both direct PCR and RTPCR are known in the art and are described in Innis et al. (1990).

The selection of PCR primers will be made according to the portions of the cDNA or gene that are to be amplified. Primers may be chosen to amplify small segments of the cDNA, the open reading frame, the entire cDNA molecule or the entire gene sequence. Variations in amplification conditions may be required to accommodate primers of differing lengths; such considerations are well known in the art and are discussed in Innis et al. (1990), Sambrook et al. (1989), and Ausubel et al (1992). By way of example only, the entire SBP2 cDNA molecule as shown in Seq. I.D. No. 5 may be amplified using the following combination of primers:

primer 1 5' TGTAAAACGACGGCCAGTGAATT 3' (Seq. I.D. No. 8)

primer 2 5' GATTACGCCAAGCTCGAAATTAA 3' (Seq. I.D. No. 9)

The open reading frame portion of the SBP2 cDNA may be amplified using the following primer pair:

primer 3 5' ATGGCGACCAGAGCCAAGCTTTCTTTA 3' (Seq. I.D. No. 10)

primer 4 5' CGCAACAGCGCGACGAC-CACGCTCGCT 3' (Seq. I.D. No. 11)

And a cDNA encoding a truncated version of the SBP2 protein (having the C-terminal 80 amino acids removed) may be amplified using the following primer pair:

primer 3 5' ATGGCGACCAGAGCCAAGCTTTCTTTA 3' (Seq. I.D. No. 10)

primer 5 5' GAAGGGATGACCAGGAGGGACAA-CAAA 3' (Seq. I.D. No. 12)

The SBP2 5 regulatory sequence may be amplified using the following primer pair:

primer 6 5' TTGTAAACGACGGCCAGTGAATT 3' (Seq. I.D. No. 13) primer 7 5' GGTGAGGTCAGT-GAGGAACAACA 3' (Seq. I.D. No. 14)

These primers are illustrative only; it will be appreciated by one skilled in the art that many different primers may be derived from the provided nucleic acid sequences in order to amplify particular regions of these molecule. Resequencing of PCR products obtained by these amplification procedures is recommended; this will facilitate confirmation of the amplified sequence and will also provide information on natural variation on this sequence in different ecotypes and plant populations.

Oligonucleotides that are derived from the SBP2 cDNA or SBP1 and SBP2 5' regulatory regions are encompassed within the scope of the present invention. Preferably, such oligonucleotide primers will comprise a sequence of at least 15–20 consecutive nucleotides of the SBP2 cDNA or gene sequences. To enhance amplification specificity, oligonucleotide primers comprising at least 25, 30, 35, 40, 45 or 50 consecutive nucleotides of these sequences may also be used.

In addition, the SBP2 gene sequence may be obtained by PCR amplification using primers derived from the disclosed cDNA sequence to probe a genomic library or genomic DNA, or by probing a genomic DNA library using a labeled probe derived from the SBP2 cDNA sequence. Standard PCR amplification or hybridization methods may be used for these approaches.

Example Two
Isolation of Homologous Gene Sequence from Other Plant Species

With the provision herein of the soybean SBP2 cDNA, SBP5' regulatory regions, and the disclosed discovery that modification of SBP proteins, particularly truncation of the C-terminus, produces enhanced sucrose uptake, the invention also enables the production of corresponding molecules from other plant species. Thus, the present invention permits the isolation of SBP2 homologs from other species, as well as the production of enhanced efficiency SBP proteins of other plant species. Both conventional hybridization and PCR amplification procedures may be utilized to obtain corresponding cDNAs from other species and to produce nucleic acids encoding enhanced activity SBP proteins. Common to both of these techniques is the hybridization of probes or primers derived from the SBP2 cDNA or gene sequence to a target nucleotide preparation, which may be, in the case of conventional hybridization approaches, a cDNA or genomic library or, in the case of PCR amplification, a cDNA or genomic library, or an mRNA preparation.

Direct PCR amplification may be performed on cDNA or genomic libraries prepared from the plant species in question, or RT-PCR may be performed using mRNA extracted from the plant cells using standard methods. PCR primers will comprise at least 15 consecutive nucleotides of the SBP2 cDNA. One of skill in the art will appreciate that sequence differences between the soybean SBP2 cDNA and the target nucleic acid to be amplified may result in lower amplification efficiencies. To compensate for this, longer PCR primers or lower annealing temperatures may be used during the amplification cycle. Where lower annealing temperatures are used, sequential rounds of amplification using nested primer pairs may be necessary to enhance specificity.

For conventional hybridization, the hybridization probe is preferably conjugated with a detectable label such as a radioactive label, and the probe is preferably of at least 20 nucleotides in length. As is well known in the art, increasing the length of hybridization probes tends to give enhanced specificity. The labeled probe derived from the soybean SBP2 cDNA or gene sequence may be hybridized to a plant cDNA or genomic library and the hybridization signal detected using means known in the art. The hybridizing colony or plaque (depending on the type of library used) is then purified and the cloned sequence contained in that colony or plaque isolated and characterized.

Homologs of the soybean SBP2 cDNA may alternatively be obtained by immunoscreening of an expression library. With the provision herein of the disclosed SBP2 nucleic acid sequences, the enzyme may be expressed and purified in a heterologous expression system (e.g., E. coli) and used to raise antibodies (monoclonal or polyclonal) specific for the SBP2 protein. Antibodies may also be raised against synthetic peptides derived from the SBP2 amino acid sequence presented herein. Methods of raising antibodies are well known in the art and are described in Harlow and Lane (1988). Such antibodies can then be used to screen an expression cDNA library produced from the plant from which it is desired to clone the SBP2 ortholog, using the methods described above. The selected cDNAs can be confirmed by sequencing and enzyme activity.

The soybean SBP2 gene or cDNA, and homologs of these sequences from other plants may be incorporated into transformation vectors and introduced into plants to modify SBP activity in such plants, as described in Example Three below. In addition, nucleic acids encoding modified SBP proteins as taught herein may also be used to produce plants having modified sucrose uptake activity. It is anticipated that the native SBP gene promoter may be particularly useful in the practice of the present invention in that it may be used to drive the expression of SBP transgenes, such as antisense constructs. By using the native SBP gene promoter, expression of these transgenes may be regulated in coordination with the native SBP gene (for example, in the same temporal or tissue-specific expression patterns).

Example Three
Transgenic Plants Having Modified Sucrose Uptake Activity

Once a gene (or cDNA) encoding a protein involved in the determination of a particular plant characteristic has been isolated, standard techniques may be used to express the cDNA in transgenic plants in order to modify that particular plant characteristic. The basic approach is to clone the EDNA into a transformation vector, such that it is operably linked to control sequences (e.g., a promoter) that direct expression of the cDNA in plant cells. The transformation vector is then introduced into plant cells by one of a number of techniques (e.g., electroporation) and progeny plants containing the introduced cDNA are selected. Preferably all or part of the transformation vector will stably integrate into the genome of the plant cell. That part of the transformation vector which integrates into the plant cell and which contains the introduced cDNA and associated sequences for controlling expression (the introduced "transgene") may be referred to as the recombinant expression cassette.

Selection of progeny plants containing the introduced transgene may be made based upon the detection of an altered phenotype. Such a phenotype may result directly from the cDNA cloned into the transformation vector or may be manifested as enhanced resistance to a chemical agent (such as an antibiotic) as a result of the inclusion of a dominant selectable marker gene incorporated into the transformation vector.

The choice of (a) control sequences and (b) how the cDNA (or selected portions of the cDNA) are arranged in the transformation vector relative to the control sequences determine, in part, how the plant characteristic affected by the introduced cDNA is modified. For example, the control sequences may be tissue specific, such that the cDNA is only expressed in particular tissues of the plant (e.g., pollen, seed) and so the affected characteristic will be modified only in those tissues. The cDNA sequence may be arranged relative to the control sequence such that the cDNA transcript is expressed normally, or in an antisense orientation. Expression of an antisense RNA corresponding to the cloned cDNA will result in a reduction of the targeted gene product (the targeted gene product being the protein encoded by the plant gene from which the introduced cDNA was derived). Overexpression of the introduced cDNA, resulting from a plus-sense orientation of the cDNA relative to the control sequences in the vector, may lead to an increase in the level of the gene product, or may result in co-suppression (also termed "sense suppression") of that gene product.

Successful examples of the modification of plant characteristics by transformation with cloned cDNA sequences are replete in the technical and scientific literature. Selected examples, which serve to illustrate the current knowledge in this field of technology, and which are herein incorporated by reference, include:

U.S. Pat. No. 5,451,514 to Boudet (modification of lignin synthesis using antisense RNA and co-suppression);

U.S. Pat. No. 5,443,974 to Hitz (modification of saturated and unsaturated fatty acid levels using antisense RNA and co-suppression);

U.S. Pat. No. 5,530,192 to Murase (modification of amino acid and fatty acid composition using antisense RNA);

U.S. Pat. No. 5,455,167 to Voelker (modification of medium chain fatty acids)

U.S. Pat. No. 5,231,020 to Jorgensen (modification of flavonoids using co-suppression);

U.S. Pat. No. 5,583,021 to Dougherty (modification of virus resistance by expression of plus-sense untranslatable RNA);

WO 96/13582 (modification of seed VLCFA composition using over expression, co-suppression and antisense RNA in conjunction with the Arabidopsis FAE1 gene); and WO 95/15387 (modification of seed VLCFA composition using over expression of jojoba wax synthesis gene).

These examples include descriptions of transformation vector selection, transformation techniques and the construction of constructs designed to over-express the introduced cDNA or to express antisense RNA corresponding to the cDNA. In light of the foregoing and the provision herein of the SBP2 gene and nucleic acids encoding modified SBP proteins conferring enhanced sucrose uptake activity, it is thus apparent that one of skill in the art will be able to introduce these nucleic acids, or homologous or derivative forms of these molecules (e.g., antisense forms), into plants in order to produce plants having modified sucrose uptake activity activity, in developing seeds and other tissues. The result can be altered plant development with agricultural and economic consequences.

a. Plant Types

Nucleic acid molecules according to the present invention (e.g., the SBP2 gene, nucleic acids encoding modified SBP proteins, homologs of these sequences and derivatives such as antisense forms) may be introduced into any plant type in order to modify sucrose uptake activity in the plant. Thus, the sequences of the present invention may be used to modify sucrose uptake activity in any higher plant, including monocotyledonous and dicotyledenous plants, including, but not limited to maize, wheat, rice, barley, soybean, beans in general, rape/canola, alfalfa, flax, sunflower, safflower, brassica, cotton, flax, peanut, clover; vegetables such as lettuce, tomato, cucurbits, potato, carrot, radish, pea, lentils, cabbage, broccoli, brussel sprouts, peppers; tree fruits such as apples, pears, peaches, apricots; flowers such as carnations and roses.

b. Vector Construction, Choice of Promoters

A number of recombinant vectors suitable for stable transfection of plant cells or for the establishment of transgenic plants have been described including those described in Pouwels et al., (1987), Weissbach and Weissbach, (1989), and Gelvin et al., (1990). Typically, plant transformation vectors include one or more cloned plant genes (or cDNAs) under the transcriptional control of 5' and 3' regulatory sequences and a dominant selectable marker. Such plant transformation vectors typically also contain a promoter regulatory region (e.g., a regulatory region controlling inducible or constitutive, environmentally-or developmentally-regulated, or cell- or tissue-specific expression), a transcription initiation start site, a ribosome binding site, an RNA processing signal, a transcription termination site, and/or a polyadenylation signal.

Examples of constitutive plant promoters which may be useful for expressing nucleic acids include: the cauliflower mosaic virus (CaMV) 35S promoter, which confers constitutive, high-level expression in most plant tissues (see, e.g., Odel et al., 1985, Dekeyser et al., 1990, Terada and Shimamoto, 1990; Benfey and Chua. 1990); the nopaline synthase promoter (An et al., 1988); and the octopine synthase promoter (Fromm et al., 1989).

A variety of plant gene promoters that are regulated in response to environmental, hormonal, chemical, and/or developmental signals, also can be used for expression of the cDNA in plant cells, including promoters regulated by: (a) heat (Callis et al., 1988; Ainley, et al. 1993; Gilmartin et al. 1992); (b) light (e.g., the pea rbcS-3A promoter, Kuhlemeier et al., 1989, and the maize rbcS promoter, Schaffner and Sheen, 1991); (c) hormones, such as abscisic acid (Marcotte et al., 1989); (d) wounding (e.g., wunI, Siebertz et al., 1989); and (e) chemicals such as methyl jasminate or salicylic acid (see also Gatz et al., 1997) can also be used to regulate gene expression.

Alternatively, tissue specific (root, leaf, flower, and seed for example) promoters (Carpenter et al., 1992; Denis et al., 1993; Opperman et al., 1993; Stockhause et al. 1997; Roshal et al., 1987; Schernthaner et al., 1988; and Bustos et al., 1989) can be fused to the coding sequence to obtained particular expression in respective organs. In addition, the timing of the expression can be controlled by using promoters such as those acting at senescencing (Gan and Amasino, 1995) or late seed development (Odell et al., 1994).

The promoter regions of the SBP1 and SBP2 genes disclosed herein confer developing seed-specific expression in soybean. Accordingly, these promoters may be used to obtain developing seed specific expression of the introduced transgene.

Plant transformation vectors may also include RNA processing signals, for example, introns, which may be positioned upstream or downstream of the ORF sequence in the transgene. In addition, the expression vectors may also include additional regulatory sequences from the 3'-untranslated region of plant genes, e.g., a 3' terminator region to increase mRNA stability of the mRNA, such as the PI-II terminator region of potato or the octopine or nopaline synthase 3' terminator regions.

Finally, as noted above, plant transformation vectors may also include dominant selectable marker genes to allow for the ready selection of transformants. Such genes include those encoding antibiotic resistance genes (e.g., resistance to hygromycin, kanamycin, bleomycin, G418, streptomycin or spectinomycin) and herbicide resistance genes (e.g., phosphinothricin acetyltransferase).

c. Arrangement of SBP sequence in vector

The particular arrangement of the SBP sequence in the transformation vector will be selected according to the type of expression of the sequence that is desired.

Where enhanced sucrose uptake activity is desired in the plant, the SBP ORF may be operably linked to a constitutive high-level promoter such as the CaMV 35S promoter. Modification of sucrose uptake activity may also be achieved by introducing into a plant a transformation vector containing a variant form of the SBP2 gene, for example a form which varies from the exact nucleotide sequence of the SBP2 ORF, but which encodes a protein that retains the functional characteristic of the SBP2 protein, i.e., conferring sucrose uptake activity. By way of example, enhanced sucrose uptake activity may also be obtained by utilizing a nucleic acid sequence encoding a modified SBP as discussed above. Such modified SBPs include SBPs having C-terminal deletions, generally in the range of 10–100 amino acid residue, and preferably about 80 amino acid residues.

In contrast, a reduction sucrose uptake activity in the transgenic plant may be obtained by introducing into plants antisense constructs based on a SBP gene sequence. For antisense suppression, SBP gene is arranged in reverse orientation relative to the promoter sequence in the transformation vector. The introduced sequence need not be the full length SBP gene, and need not be exactly homologous to the SBP gene found in the plant type to be transformed. Generally, however, where the introduced sequence is of shorter length, a higher degree of homology to the native SBP sequence will be needed for effective antisense suppression. Preferably, the introduced antisense sequence in the vector will be at least 30 nucleotides in length, and improved antisense suppression will typically be observed as the length of the antisense sequence increases. Preferably, the length of the antisense sequence in the vector will be greater than 100 nucleotides. Transcription of an antisense construct as described results in the production of RNA molecules that are the reverse complement of mRNA molecules transcribed from the endogenous SBP gene in the plant cell. Although the exact mechanism by which antisense RNA molecules interfere with gene expression has not been elucidated, it is believed that antisense RNA molecules bind to the endogenous mRNA molecules and thereby inhibit translation of the endogenous mRNA.

Suppression of endogenous SBP gene expression can also be achieved using ribozymes. Ribozymes are synthetic RNA molecules that possess highly specific endoribonuclease activity. The production and use of ribozymes are disclosed in U.S. Pat. No. 4,987,071 to Cech and U.S. Pat. No. 5,543,508 to Haselhoff. The inclusion of ribozyme sequences within antisense RNAs may be used to confer RNA cleaving activity on the antisense RNA, such that endogenous mRNA molecules that bind to the antisense RNA are cleaved, which in turn leads to an enhanced antisense inhibition of endogenous gene expression.

Constructs in which a SBP nucleic acid (or variants thereof) are over-expressed may also be used to obtain co-suppression of the endogenous SBP gene in the manner described in U.S. Pat. No. 5,231,021 to Jorgensen. Such co-suppression (also termed sense suppression) does not require that the SBP gene be introduced into the plant cells, nor does it require that the introduced sequence be exactly identical to the endogenous SBP gene. However, as with antisense suppression, the suppressive efficiency will be enhanced as (1) the introduced sequence is lengthened and (2) the sequence similarity between the introduced sequence and the endogenous SBP gene is increased.

Constructs expressing an untranslatable form of a SBP mRNA may also be used to suppress the expression of endogenous SBP activity. Methods for producing such constructs are described in U.S. Pat. No. 5,583,021 to Dougherty et al. Preferably, such constructs are made by introducing a premature stop codon into the SBP ORF.

Finally, dominant negative mutant forms of the disclosed sequences may be used to block endogenous SBP activity. Such mutants require the production of mutated forms of the SBP protein that bind to sucrose but do not catalyze the uptake of sucrose.

d. Transformation and Regeneration Techniques

Transformation and regeneration of both monocotyledonous and dicotyledonous plant cells is now routine, and the selection of the most appropriate transformation technique will be determined by the practitioner. The choice of method will vary with the type of plant to be transformed; those skilled in the art will recognize the suitability of particular methods for given plant types. Suitable methods may include, but are not limited to: electroporation of plant protoplasts; liposome-mediated transformation; polyethylene glycol (PEG) mediated transformation; transformation using viruses; micro-injection of plant cells; micro-projectile bombardment of plant cells; vacuum infiltration; and *Agrobacterium tumeficiens* (AT) mediated transformation. Typical procedures for transforming and regenerating plants are described in the patent documents listed at the beginning of this section.

e. Selection of Transformed Plants

Following transformation and regeneration of plants with the transformation vector, transformed plants are preferably selected using a dominant selectable marker incorporated into the transformation vector. Typically, such a marker will confer antibiotic resistance on the seedlings. of transformed plants, and selection of transformants can be accomplished by exposing the seedlings to appropriate concentrations of the antibiotic.

After transformed plants are selected and grown to maturity, they can be assayed using known methods to determine whether SBP activity has been altered as a result of the introduced transgene. In addition, antisense or sense suppression of an endogenous SBP gene may be detected by analyzing mRNA expression on Northern blots.

Example Four

Production of Sequence Variants

As noted above, modification of sucrose uptake activity in plant cells can be achieved by transforming plants with the SBP2 cDNA or gene, antisense constructs based on the SBP2 cDNA or gene sequence or nucleic acid sequences encoding modified SBP proteins. With the provision of the SBP2 cDNA and gene sequences and the SBP 5' regulatory regions herein, the creation of variants on these sequences by standard mutagenesis techniques is now enabled.

Variant DNA molecules include those created by standard DNA mutagenesis techniques, for example, M13 primer mutagenesis. Details of these techniques are provided in Sambrook et al. (1989), Ch. 15. By the use of such techniques, variants may be created which differ in minor ways from the disclosed sequences disclosed. DNA molecules and nucleotide sequences which are derivatives of those specifically disclosed herein and which differ from those disclosed by the deletion, addition or substitution of nucleotides while still encoding a protein which possesses the functional characteristic of a SBP protein (i.e., the ability to mediate sucrose uptake in the yeast assay system) are comprehended by this invention. DNA molecules and nucleotide sequences which are derived from the SBP2 cDNA and gene sequences disclosed include DNA sequences which hybridize under stringent conditions to the DNA sequences disclosed, or fragments thereof.

Hybridization conditions resulting in particular degrees of stringency will vary depending upon the nature of the hybridization method of choice and the composition and length of the hybridizing DNA used. Generally, the temperature of hybridization and the ionic strength (especially the $Na^+$ concentration) of the hybridization buffer will determine the stringency of hybridization. Calculations regarding hybridization conditions required for attaining particular degrees of stringency are discussed by Sambrook et al. (1 989), chapters 9 and 11, herein incorporated by reference. By way of illustration only, a hybridization experiment may be performed by hybridization of a DNA molecule (for example, soybean SBP2 cDNA sequence) to a target DNA molecule (for example, the a corresponding SBP2 cDNA sequence in tobacco) which has been electrophoresed in an agarose gel and transferred to a nitrocellulose membrane by Southern blotting (Southern, 1975), a technique well known in the art and described in (Sambrook et al., 1989). Hybridization with a target probe labeled with [$^{32}$P]dCTP is generally carried out in a solution of high ionic strength such as 6×SSC at a temperature that is 20–25° C. below the melting temperature, $T_m$, described below. For such Southern hybridization experiments where the target DNA molecule on the Southern blot contains 10 ng of DNA or more, hybridization is typically carried out for 68 hours using 12 ng/ml radiolabeled probe (of specific activity equal to $10^9$ CPM/μg or greater). Following hybridization, the nitrocellulose filter is washed to remove background hybridization. The washing conditions should be as stringent as possible to remove background hybridization but to retain a specific hybridization signal. The term $T_m$ represents the temperature above which, under the prevailing ionic conditions, the radiolabeled probe molecule will not hybridize to its target DNA molecule. The $T_m$ of such a hybrid molecule may be estimated from the following equation (Bolton and McCarthy, 1962):

$$T_m = 81.5C\ 16.6(\log_{10}[Na^+]) + 0.41(\%G+C) - 0.63(\%\ formamide)(600/l)$$

Where l=the length of the hybrid in base pairs.
This equation is valid for concentrations of $Na^+$ in the range of 0.01 M to 0.4 M, and it is less accurate for calculations of $T_m$ in solutions of higher $[Na^+]$. The equation is also primarily valid for DNAs whose G+C content is in the range of 30% to 75%, and it applies to hybrids greater than 100 nucleotides in length (the behavior of oligonucleotide probes is described in detail in Ch. 11 of Sambrook et al., 1989).

Thus, by way of example, for a 150 base pair DNA probe derived from the first 150 base pairs of the open reading frame of the soybean SBP2 cDNA (with a hypothetical % GC=45%), a calculation of hybridization conditions required to give particular stringencies may be made as follows:

For this example, it is assumed that the filter will be washed in 0.3×SSC solution following hybridization, thereby $[Na^+]=0.045M$; % GC=45%; Formamide concentration=0; l=150 base pairs; and $T_m=81.5\ 16(\log_{10}[Na^+])+(0.41\times 45)\ (600/150)$ and so $T_m=74.4$ C.

The $T_m$ of double-stranded DNA decreases by 1–1.5° C. with every 1% decrease in homology (Bonner et al., 1973). Therefore, for this given example, washing the filter in 0.3×SSC at 59.4–64.4° C. will produce a stringency of hybridization equivalent to 90%. Alternatively, washing the hybridized filter in 0.3×SSC at a temperature of 65.4–68.4° C. will yield a hybridization stringency of 94%. The above example is given entirely by way of theoretical illustration. One skilled in the art will appreciate that other hybridization techniques may be utilized and that variations in experimental conditions will necessitate alternative calculations for stringency.

DNA sequences from plants that encode a protein having SBP activity and which hybridize under hybridization conditions of at least 75%, more preferably at least 80%, more preferably at least 85%, more preferably at least 90% and most preferably at least 95% stringency to the disclosed SBP2 sequence are encompassed within the present invention.

The degeneracy of the genetic code further widens the scope of the present invention as it enables major variations in the nucleotide sequence of a DNA molecule while maintaining the amino acid sequence of the encoded protein. For example, the second amino acid residue of the soybean SBP2 protein is alanine.

This is encoded in the soybean SBP2 open reading frame by the nucleotide codon triplet GCG. Because of the degeneracy of the genetic code, three other nucleotide codon triplets-GCA, GCC and GCT-also code for alanine. Thus, the nucleotide sequence of the soybean SBP2 ORF could be changed at this position to any of these three codons without affecting the amino acid composition of the encoded protein or the characteristics of the protein. Based upon the degeneracy of the genetic code, variant DNA molecules may be derived from the cDNA and gene sequences disclosed herein using standard DNA mutagenesis techniques as described above, or by synthesis of DNA sequences. Thus, this invention also encompasses nucleic acid sequences which encode a SBP protein but which vary from the disclosed nucleic acid sequences by virtue of the degeneracy of the genetic code.

The present invention teaches that enhanced sucrose uptake activity may be obtained by modifying the sequence of a plant SBP, e.g., by deleting 80 C-terminal amino acids. One skilled in the art will recognize that DNA mutagenesis techniques may be used not only to produce variant DNA molecules, but will also facilitate the production of such modified SBP protein. In addition, other changes to the amino acid sequence can be made including deletions, additions and substitutions.

While the site for introducing an amino acid sequence variation is predetermined, the mutation per se need not be predetermined. For example, in order to optimize the performance of a mutation at a given site, random mutagenesis may be conducted at the target codon or region and the expressed protein variants screened for the optimal combination of desired activity. Techniques for making substitution mutations at predetermined sites in DNA having a known sequence as described above are well known.

Amino acid substitutions are typically of single residues; insertions usually will be on the order of about from 1 to 10 amino acid residues; and deletions will range about from 1 to more than 100 residues. Substitutions, deletions, insertions or any combination thereof may be combined to arrive at a final construct. Obviously, the mutations that are made in the DNA encoding the protein must not place the sequence out of reading frame and preferably will not create complementary regions that could produce secondary mRNA structure.

Substitutional variants are those in which at least one residue in the amino acid sequence has been removed and a different residue inserted in its place. Such substitutions generally are made in accordance with the following Table 1 when it is desired to finely modulate the characteristics of the protein. Table 1 shows amino acids which may be substituted for an original amino acid in a protein and which are regarded as conservative substitutions.

TABLE 1

| Original Residue | Conservative Substitutions |
|---|---|
| Ala | ser |
| Arg | lys |
| Asn | gln; his |
| Asp | glu |
| Cys | ser |
| Gln | asn |
| Glu | asp |
| Gly | pro |
| His | asn; gln |
| Ile | leu, val |

TABLE 1-continued

| Original Residue | Conservative Substitutions |
|---|---|
| Leu | ile; val |
| Lys | arg; gln; glu |
| Met | leu; ile |
| Phe | met; leu; tyr |
| Ser | thr |
| Thr | ser |
| Trp | tyr |
| Tyr | trp; phe |
| Val | ile; leu |

Substantial changes in enzymatic function or other features are made by selecting substitutions that are less conservative than those in Table 1, i.e., selecting residues that differ more significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. The substitutions which in general are expected to produce the greatest changes in protein properties will be those in which (a) a hydrophilic residue, e.g., seryl or threonyl, is substituted for (or by) a hydrophobic residue, e.g., leucyl, isoleucyl, phenylalanyl, valyl or alanyl; (b) a cysteine or proline is substituted for (or by) any other residue; (c) a residue having an electropositive side chain, e.g., lysyl, arginyl, or histadyl, is substituted for (or by) an electronegative residue, e.g., glutamyl or aspartyl; or (d) a residue having a bulky side chain, e.g., phenylalanine, is substituted for (or by) one not having a side chain, e.g., glycine.

The effects of these amino acid substitutions or deletions or additions may be assessed for derivatives of the SBP proteins by analyzing the ability of the derivative proteins to catalyze sucrose uptake in the yeast assay system described above.

Example Five
Use of SBP 5' Regulatory Regions to Control Transgene Expression

The promoters of the Glycine SBP1 and SBP2 genes confer developing seed-specific expression. Accordingly, the promoter sequences, shown in Seq. I.D. Nos. 7 (SBP2) and 8 (SBP1) may be used to produce transgene constructs that are specifically expressed in developing seeds. One of skill in the art will recognize that regulation of transgene expression in developing seeds may be achieved with less than the entire 5' regulatory sequences shown in Seq. I.D. Nos. 7 & 8. Thus, by way of example, developing seed-specific expression may be obtained by employing a 50 base pair or 100 base pair region of the disclosed promoter sequences. The determination of whether a particular sub-region of the disclosed sequence operates to confer effective seed-specific expression in a particular system (taking into account the plant species into which the construct is being introduced, the level of expression required, etc.) will be performed using known methods, such as operably linking the promoter sub-region to a marker gene (e.g. GUS), introducing such constructs into plants and then determining the level of expression of the marker gene in developing seeds and other plant tissues.

The present invention therefore facilitates the production, by standard molecular biology techniques, of nucleic acid molecules comprising the SBP1 or SBP2 promoter sequence operably linked to a nucleic acid sequence, such as an open reading frame. Suitable open reading frames include open reading frames encoding any protein for which expression in developing seeds is desired. Examples of genes that may suitably be expressed in a seed-specific manner under the control of the disclosed SBP promoters include, but are not limited to:

(1) genes that enhance the nutritional quality of the seeds, for example, by increasing the content of limiting amino acids, including lysine, methionine and cysteine. This may be achieved by expressing proteins containing high levels of these amino acids in seeds. Examples include the high methionine storage proteins from brazil nut (Saalbach et al., 1996) and sunflower (Molvig et al., 1997).

(2) genes that increase gluten levels in wheat, so as to enhance the bread-making quality of the wheat flour (Shewry et al., 1995).

(3) genes that enhance insect resistance in the seed (for example, resistance to weevils). Suitable genes include the α-amylase inhibitor gene which kills seed weevils (Schmidt, 1994).

REFERENCES

Ainley et al. (1993) *Plant Mol. Biol.* 22:13—23.
Altschul & Gish. (1996) *Methods Enzymol.*, 266, 460–80.
Altschul et al. (1990) Basic local alignment search tool. *J. Mol. Biol.* 215:403–410.
Altschul et al. (1994) *Nature Genet.*, 6, 119–29.
An et al. (1988) *Plant Physiol.* 88:547.
Ausubel et al. (1987) In *Current Protocols in Molecular Biology*, Greene Publishing Associates and Wiley-Intersciences.
Ausubel et al. eds., *Current Protocols in Molecular Biology*, John Wiley and Sons, New York, 1994.
Benfey & Chua (1990) *Science* 250:959–966.
Birch et al. (1997) *Ann. Rev. Plant Physiol. Plant Mol. Biol.* 48:297–326.
Bolton & McCarthy (1962) *Proc. Natl. Acad. Sci. USA* 48:1390.
Bonner et al. (1973) *J. Mol. Biol.* 81:123.
Bush (1993) *Ann. Rev. Plant Physiol. Plant Mol. Biol.* 44:513542.
Bustos et al. (1989) *Plant Cell* 1:839.
Callis et al. (1988) *Plant Physiol.* 88:965.
Carpenter et al. (1992) *The Plant Cell* 4:557–571.
Corpet et al. (1988) *Nucleic Acids Research* 16, 10881–90
Dekeyser et al. (1990) *Plant Cell* 2:591.
Denis et al. (1993) *Plant Physiol.* 101:1295–1304.
Fromm et al. (1989) *Plant Cell* 1:977.
Gan & Amansino (1995) *Science* 270:1986–1988.
Gatz et al. (1997) *Ann. Rev. Plant Physiol. Plant Mol. Biol.* 48:89–108.
Gelvin et al. (1990) *Plant Molecular Biology Manual*, Kluwer Academic Publishers.
Gietz et al. (1992) *Nuc. Acids Res.* 20:1425.
Gilmartin et al. (1992) *The Plant Cell* 4:839–949.
Grimes et al. (1992) *Plant Cell* 4:15611574.
Harlow & Lane (1988) *Antibodies, A Laboratory Manual*, Cold Spring Harbor Laboratory, New York.
Higgins & Sharp (1988) *Gene,* 73: 237–244
Higgins & Sharp (1989) *CABIOS* 5: 151–153
Huang et al. (1992) *Computer Applications in the Biosciences* 8, 155–65
Innis et al. (1990) *PCR Protocols, A Guide to Methods and Applications,* Innis et al. (eds.), Academic Press, Inc., San Diego, Calif.
Kawasaki et al. (1990). In *PCR Protocols, A Guide to Methods and Applications,* Innis et al. (eds.), 2127, Academic Press, Inc., San Diego, Calif.

Kuhlemeier et al. (1989) *Plant Cell* 1: 471.
Meyer & Horgan (1996) *Ann. Rev. Plant Physiol. Plant Mol. Biol.* 47:23–48.
Meyers & Miller (1988) *Computer Applic. Biol. Sci.,* 4: 11–17.
Molvig et al. (1997) *Proc. Natl. Acad. Sci.* 94:8393–8398.
Needleman & Wunsch (1970) *J. Mol. Biol.* 48: 443
Odel et al. (1985) *Nature* 313:810.
Odell et al. (1994). *Plant Physiol.* 106:447–458.
Opperman et al. (1993) *Science* 263:221–223.
Overvoorde & Grimes (1994) *J. Biol Chem.* 269:1515415161.
Overvoorde et al. (1996) *Plant Cell* 8:271280.
Pearson & Lipman (1988) *Proc. Natl. Acad. sci. USA* 85: 2444
Pearson et al. (1994) *Methods in Molecular Biology* 24, 307–31.
Pouwels et al. (1987) *Cloning Vectors: A Laboratory Manual,* 1985, supp.
Riesmeier et al. (1992) *EMBO J.* 11:47054713.
Ripp et al. (1988) *Plant Physiol.* 88:14351445.
Roshal et al. (1987). *EMBO J.* 6:1155.
Saalbach et al. (1996) *Plant Physiol.* 112:975–985.
Sambrook et al. (1989) In *Molecular Cloning: A Laboratory Manual,* Cold Spring Harbor, N.Y.
Schaffner & Sheen (1991) *Plant Cell* 3:997.
Schernthaner et al. (1988) *EMBO J.* 7:1249.
Schmidt (1994) *Science* 265:739
Shewry et al. (1995) *The Plant Cell* 7:945–956.
Siebertz et al. (1989) *Plant Cell* 1:961.
Smith & Waterman (1981) *Adv. Appl. Math.* 2: 482
Southern (1975). *J. Mol. Biol.* 98:503.
Southern et al. (1982) *J. Mol. Appl. Genet.* 1:327341.
Stockhause et al. (1997) *The Plant Cell* 9:479–489.
Terada & Shimamoto (1990) *Mol. Gen. Genet.* 220:389.
Tijssen (1993) *Laboratory Techniques in Biochemistry and Molecular Biology— Hybridization with Nucleic Acid Probes* Part I, Chapter 2 "Overview of principles of hybridization and the strategy of nucleic acid probe assays", Elsevier, N.Y.
Weissbach & Weissbach (1989) Methods for Plant Molecular Biology, Academic Press.

---

What is claimed is:

1. An isolated nucleic acid molecule-encoding an amino acid sequence selected from the group consisting of:
   (a) SEQ ID NO: 3;
   (b) SEQ ID NO: 4; and
   (c) amino acid sequences having at least 90% sequence identity with the amino acid sequence of (a), or (b),
   wherein the nucleic acid encodes a plant proton-independent sucrose-binding protein, and wherein expression of the plant proton-independent sucrose-binding protein in an assay system confers sucrose uptake on the system.

2. A recombinant nucleic acid molecule comprising a promoter sequence operably linked to the nucleic acid molecule of claim 1.

3. A transgenic plant comprising the recombinant nucleic acid molecule of claim 2.

4. A vector comprising a nucleic acid molecule according to claim 1.

* * * * *